(12) United States Patent
Liu

(10) Patent No.: US 8,313,458 B2
(45) Date of Patent: *Nov. 20, 2012

(54) BARREL TYPE PLUNGER FOR USE WITH A NEEDLE-RETRACTABLE SAFETY SYRINGE AND THE SYRINGE USING THE SAME

(76) Inventor: Wenjie Liu, Beijing (CN)

( * ) Notice: Subject to any disclaimer, the term of this patent is extended or adjusted under 35 U.S.C. 154(b) by 208 days.

This patent is subject to a terminal disclaimer.

(21) Appl. No.: 12/832,365

(22) Filed: Jul. 8, 2010

(65) Prior Publication Data

US 2010/0286622 A1 Nov. 11, 2010

Related U.S. Application Data

(63) Continuation-in-part of application No. 12/057,656, filed on Mar. 28, 2008, now Pat. No. 7,789,855.

(30) Foreign Application Priority Data

Mar. 30, 2007 (CN) .......................... 2007 1 0090989

(51) Int. Cl.
*A61M 5/00* (2006.01)
(52) U.S. Cl. ........................................................ 604/110
(58) Field of Classification Search .................... 604/110
See application file for complete search history.

(56) References Cited

U.S. PATENT DOCUMENTS

| | | | | |
|---|---|---|---|---|
| 4,927,414 A | * | 5/1990 | Kulli | 604/110 |
| 5,578,015 A | * | 11/1996 | Robb | 604/195 |
| 6,206,857 B1 | * | 3/2001 | Chen | 604/195 |
| 6,641,555 B1 | * | 11/2003 | Botich et al. | 604/110 |
| 6,676,638 B2 | * | 1/2004 | Takagi et al. | 604/167.03 |
| 6,689,102 B2 | * | 2/2004 | Greene | 604/164.08 |
| 6,692,471 B2 | * | 2/2004 | Boudreaux | 604/198 |
| 6,942,652 B1 | * | 9/2005 | Pressly et al. | 604/508 |
| 7,331,936 B2 | * | 2/2008 | Liu | 604/110 |

(Continued)

FOREIGN PATENT DOCUMENTS

EP 1 716 880 A2 11/2006
(Continued)

OTHER PUBLICATIONS

EP Search Report dated Jul. 7, 2008 issued in EP Application No. 08005025.5.

*Primary Examiner* — Nicholas Lucchesi
*Assistant Examiner* — Diva K Chander
(74) *Attorney, Agent, or Firm* — Sughrue Mion, PLLC

(57) ABSTRACT

The present invention provides a needle-retractable safety including an improved barrel type plunger, including a barrel, a needle retracted trigger and a supporting member. A front portion of the barrel is fitted over a sealing rubber pad, a slotted hole is disposed at a wall of the front portion of the barrel, a bearing piece is provided in the slotted hole, and one end of the bearing piece is connected to the front side wall of the slotted hole. The barrel and supporting member are provided with a snap-in structure, respectively, which make supporting member releasably engaged in said barrel. The supporting member is able to translate backwards under the action of a needle retraction force so that said bearing piece can be returned to such a position that said needle can be retracted backwards to the interior of the barrel.

11 Claims, 14 Drawing Sheets

U.S. PATENT DOCUMENTS

| | | | |
|---|---|---|---|
| 7,713,243 B2 * | 5/2010 | Hillman | 604/192 |
| 7,731,678 B2 * | 6/2010 | Tennican et al. | 604/88 |
| 7,789,855 B2 * | 9/2010 | Liu | 604/110 |
| 2003/0060760 A1 * | 3/2003 | Botich et al. | 604/110 |
| 2004/0215150 A1 * | 10/2004 | Shue et al. | 604/192 |
| 2010/0286622 A1 * | 11/2010 | Liu | 604/196 |

FOREIGN PATENT DOCUMENTS

| | | |
|---|---|---|
| WO | 99/53979 A1 | 10/1999 |
| WO | 2005/058398 A1 | 6/2005 |

* cited by examiner

BARREL TYPE PLUNGER FOR USE WITH A NEEDLE-RETRACTABLE SAFETY SYRINGE AND THE SYRINGE USING THE SAME

This is a Continuation-In-Part of application Ser. No. 12/057,656 filed on Mar. 28, 2008. The entire disclosure of the prior application, application Ser. No. 12/057,656 is hereby incorporated by reference.

TECHNICAL FIELD

The present invention relates to a medical instrument, particularly to an improved barrel type plunger for use with a needle-retractable safety syringe and a syringe containing the above-mentioned barrel type plunger.

BACKGROUND ART

Syringes are commonly and largely used in the field of medical treatment. If the syringes are used repeatedly, it is likely to cause the diseases to spread among the different patients and result in cross infection which will endanger the health of the public people. In order to seek illegal gains, some persons collect the used and discard disposable syringes and put these syringes into the medical treatment market again. As a result, it will be a heavy threaten of spreading and proliferating many diseases. On the other hand, healthcare workers and the waste collecting persons may suffer from needlesticks after the completion of injection because of the expose of the needle heads so as to cause disease infections or spread.

In order to prevent repeatedly using the syringes and to make the syringes self-destruct immediately once they have been used so that the syringes can actually be used only one time and accidental needlesticks caused by the used syringes can be prevented from occurring, a solution concerning a needle-retractable disposable syringe has been proposed. Also, an improvement on the barrel type plunger used for this kind of syringe has been made so that the self-destruction of the syringes and the controllability of the needle retraction can be obtained.

As an example, Chinese utility model patent ZL200520015704.2 discloses a novel barrel type plunger used for a needle-retractable safety syringe and a safety syringe using with the same. As described in this Chinese patent, the bearing piece is controlled by the fitting of the outer barrel and the inner barrel of the barrel type plunger, and the bearing piece is used to control the retraction of the pushing post and the released needle carrier. In this way, the self-destruction of the syringes after the completion of injection and the controllability of the needle retraction can be realized. Moreover, it can prevent the syringes from being used repeatedly, and can eliminate a risk of accidental needlesticks caused by the exposed syringes needle after the completion of injection.

Although the solution as disclosed in the above-mentioned Chinese utility model patent can realize the controllability of the syringe needle retraction after the injection, this solution has the following defects: (1) the structure of the barrel type plunger is relatively complex so that it is rather difficult for the barrel type plunger to be produced and the assembling procedure is relatively complex, thereby the production cost is relatively high; (2) since the structure of the barrel type plunger is relatively complex, it is hardly to be suitable for a syringe having minor milliliter volume, such as 1 ml syringe.

Further, since the vaccine for injection can not be in contact with the plastic materials commonly used for manufacturing syringes for a long term and vaccine is generally pre-filled in a syringe before injection according to the practice of vaccine injection, said disclosed technical solution also can not be applied to the pre-filled-vaccine injection.

DISCLOSURE OF THE INVENTION

In order to overcome the above-mentioned disadvantages present in the prior art, an object of the present invention is to provide a barrel type plunger which has simple structure, is easy to produce and assemble, and can make a needle to be retracted under the control, and to provide a syringe which is equipped with the barrel type plunger. Another object of the present invention is to provide a syringe which is equipped with the above-mentioned barrel type plunger and can be pre-filled and encapsulated with vaccine before injection.

According to one respect of the invention, the present invention provides an improved barrel type plunger for use with a needle-retractable safety syringe, comprising a barrel, a needle retracted trigger and a supporting member, a front portion of said barrel is fitted with a sealing rubber pad, wherein a slotted hole is provided at a wall of the front portion of said barrel, a bearing piece is provided in said slotted hole, one end of said bearing piece is connected to the front side wall of said slotted hole; during the assembly, said bearing piece is deflected laterally towards the interior of said barrel in a resettable manner in order to support said needle retracted trigger; said needle retracted trigger is provided at a front end of a cavity of said barrel and is supported on said bearing piece which has been deflected laterally; said supporting member is provided in said barrel, the front end of which supports said bearing piece which has been deflected laterally, and the rear end of which is provided with a base for sealing the opening at the rear end of said barrel; said barrel and said supporting member are provided with a snap-in structure respectively, which can be engaged cooperatively with each other; during the assembly, said supporting member is releasably engaged in said barrel; and after having released from said barrel, said supporting member is able to translate backwards under the action of a needle retraction force so that said bearing piece can be returned to such a position that said needle retracted trigger and said needle can be retracted backwards to the interior of said barrel.

In a preferable embodiment of the present invention, said needle retracted trigger is a pushing post having a closed front portion; after the assembly, the front end of said pushing post is projected beyond an opening of the barrel cavity formed at the front end of said barrel and said sealing rubber pad, and the projected portion is in a shape of a tubular structure with a flush end or in a shape of a tubular structure having an end with longitudinally extending gear-like projections.

In another exemplary embodiment of the invention, said supporting member is in a shape of barrel body having an opened front end and a closed rear end, the wall of the rear portion of said barrel body is disposed with at least one opening, a flexible rib extends forwardly along the axial direction of said barrel body from the rear inner wall each said opening, an outer wall of said flexible rib is formed with a first projection which is in a shape of semi-sphere, triangle or other shapes having a slanted top end surface; the wall of said barrel is provided with a window at a position which corresponds to the position of said first projection; and during the assembly, said first projection is supported at the rear edge of said window and is projecting beyond said window so that said supporting member can be releasably engaged with said barrel.

In a further exemplary embodiment of the invention, a notch adapted for restoring said bearing piece is formed on the wall of the front end portion of said supporting member at a position corresponding to the home position of said bearing piece; and said openings and said windows are in a number of two and are disposed opposite to each other, each of said openings has a flexible rib therein, one first projection is provide on the outer wall of each of said flexible ribs at the same level.

In a further exemplary embodiment of the invention, said slotted hole provided on the wall of the front portion of said barrel extends toward the middle-rear part of said barrel, and an slotted hole is formed on the wall of said barrel opposed to said slotted hole; said supporting member includes the base, two flexible ribs and two first projections, said two flexible ribs are disposed oppositely on the front end surface of said base and is extending forwardly along the axial direction of said barrel, the arrangement of said flexible ribs are set in such a manner that said flexible ribs can be engaged with said two slotted holes, respectively, said two first projections are provided on the outer walls of said two flexible ribs, respectively, and are in a shape of semi-sphere, triangle or other shapes having a slanted top end surface; during the assembly, said two first projections are supported at the rear edge of said two slotted holes, respectively, and are projecting beyond said slotted holes so that said supporting member can be releasably engaged in said barrel; and said bearing piece is supported by the front end of at least one of said flexible ribs after it has been deflected laterally.

In a further preferably embodiment of the invention, on the wall of the middle-rear part of said barrel is provided with two opposed windows; said supporting member includes the base, two flexible ribs and a supporting bar, said flexible ribs and the supporting bar are all disposed on the front end surface of said base and extend forwardly along the axial direction of said barrel, the outer walls of said two flexible ribs are provided with a first projection, respectively, which is in a shape of semi-sphere, triangle or other shapes having a slanted top end surface, the length of said supporting bar is suitable to a position where said bearing piece is in the cavity of the barrel after it has been deflected laterally, the arrangement orientation of the supporting bar on the base is set to match to the arrangement orientation of said bearing piece so that said bearing piece is supported by the front end of said supporting bar after it has been deflected laterally; and during the assembly, said first projections are supported at the rear edges of said windows and are projecting beyond said windows so that said supporting member can be releasably engaged in said barrel.

In a further preferably embodiment of the invention, a projected retaining ring is provided in a circle along the inner wall of the rear portion of said barrel so that said supporting member will be blocked by said retaining ring again after it has been moved backwards to such an extent that said bearing piece has returned to its home position.

In a further preferably embodiment of the invention, the outer wall of said flexible rib is further provided with a second projection thereon, which is arranged behind said first projection, the distance between the rear end surface of said first projection and the rear end surface of said second projection is set to be equal to or larger than the backward movement distance of said supporting member required for returning said bearing piece to the position where said pushing post and the needle can be retracted back to the interior of said barrel, and the projecting height of said second projection is set to be smaller than or equal to the projecting height of said first projection; and during the assembly, said first projection and said second projection are mounted in the window and extend beyond the same, said second projection is supported by the rear edge of said window so that said supporting member can be releasably engaged in said barrel.

In a further preferably embodiment of the invention, at least one window is formed on the wall of the middle-rear part of said barrel; said supporting member is in a shape of barrel body having an opened front end and a closed rear end, the opening is formed on the wall of the middle-rear portion of said barrel body at a position corresponding to the position of each of window, a flexible rib extending backwards along the axial direction of said barrel body are formed on the front side wall of said opening, an outer wall of said flexible rib is formed with a first projection thereon, which is in a shape of semi-sphere, triangle or other shapes having a slanted top end surface; and during the assembly, said first projection (601) is supported at the rear edge of said window and is projecting beyond said window so that said supporting member can be releasably engaged with said barrel.

In a further preferably embodiment of the invention, a notch adapted for restoring said bearing piece is provided on the wall of the front end portion of said barrel-like supporting member at a position corresponding to the home position of said bearing piece, the windows formed on the wall of said barrel and the openings on the wall of said barrel-like supporting member are in a number of two and are substantially symmetrical, respectively, said flexible bars and said first projections provided thereon are in two sets and are substantially symmetrical, respectively; each of said flexible bar is further provided with a second projection thereon, which is arranged behind said first projection, the distance between the rear end surface of said first projection and the rear end surface of said second projection is set to be equal to or larger than the backward movement distance of said barrel-like supporting member required for returning said bearing piece to the position where said pushing post and the needle can be retracted back to the interior of said barrel, and the projection height of said second projection is set to be smaller than or equal to the projection height of said first projection; and during the assembly, said first projection and said second projection are all mounted in the window and extend beyond the same, said second projection is supported by the rear edge of said window so that said supporting member can be releasably engaged in said barrel.

In a further preferably embodiment of the invention, said supporting member is composed of a front barrel and a rear barrel which are nested one on the top of another; a notch adapted for restoring said bearing piece is formed on the wall of a front end portion of said front barrel at a position which corresponds to the home position of said bearing piece, the rear end of said front barrel and the front end of said rear barrel are provided with a socket and spigot joint, respectively, which can be engaged to each other; said opening is formed on the wall of said rear barrel behind the portion which is jointed to said front barrel.

In a further preferably embodiment of the invention, the outer diameter of the portion at the front end of said rear barrel which is joined to said front barrel is set to be smaller than the outer diameter of the other portions of said rear barrel and match to the inner diameter of said front barrel, a set piece is disposed on a portion at the front end of said rear barrel which is joined to said front barrel; a locating slot or locating hole adapted for fitting to said set piece is formed on the wall of the rear end portion of said front barrel at a portion which is joined to said rear barrel; a second projection is formed behind said first projection, the projecting height of said first projection is set to be larger than or equal to the projecting height of said second projection, and the distance between the rear end surface of said first projection and the rear end surface of said second projection is set to be equal to or larger than the backward movement distance of said supporting member required for returning said bearing piece to the position where said pushing post and the needle can be retracted back to the interior of said barrel; and during the assembly, said first projection and said second projection are all mounted in the window and extend beyond the same, said second projection is supported by the rear edge of said window so that said supporting member can be releasably engaged in said barrel.

In a further preferably embodiment of the invention, the barrel type plunger for use with a needle-retractable safety syringe further comprises a protective sleeve, said protective sleeve includes a thicker tubing and a thinner tubing which are connected together; the inner diameter of said thicker tubing is set to be larger than or equal to the outer diameter of the barrel of the syringe; a flange is formed in a circle on the outer wall of the rear portion of said barrel; the inner diameter of said thinner tubing is set to match to the outer diameter of said barrel, and a recess which can be engaged to said flange is formed in a circle on the inner wall of said thinner tubing; and during the assembly, said protective sleeve is fitted to the rear end of said barrel and is secured thereon by means of the engagement of said recess and said flange so that the thicker tubing surrounds the engaged portion where said barrel and said supporting member are engaged to each other.

In a further preferably embodiment of the invention, the barrel type plunger for use with a needle-retractable safety syringe further comprises a sealing pad and a compressible needle stop member, said sealing pad is mounted between the walls of said pushing post and the front end of said barrel; the front portion of said pushing post is provided with a chamber, in which said needle stop member is disposed, the leading end of said needle stop member projects beyond the front end of said pushing post after it has blocked the opening of the chamber of said pushing post.

In a further preferably embodiment of the invention, a tubular front end portion with a flush end or with an end having longitudinally extending gear-like protrusions is exposed after said barrel is fitted with said sealing rubber pad; said pushing post can be replaced with a compressible needle stop member which includes a stop post and a spring fitted over the rear portion of said stop post and supporting said stop post; the cavity provided at the front end of said barrel for arranging said needle stop member includes a front chamber and a rear chamber, the inner diameter of said front chamber is set to match to the outer diameter of said stop post, and the inner diameter of said rear chamber is set to be larger than the outer diameter of said stop post; a recess is formed in a circle on the portion of said stop post corresponding said front chamber, a sealing ring is disposed in said recess, a projected orientation ring is formed in at least one circle on such a portion of said stop post corresponding to said rear chamber, the outer diameter of said orientation ring is set to match to the inner diameter of said rear chamber; the leading end of said needle stop member projects out of the front end of said barrel after it has blocked the opening at the front end of said barrel, and the rear end of said needle stop member can be compressed and is supported on said bearing piece; the front end surface of said stop post is provided with a recess; and the wall of the tubular front end portion of said barrel is also provided with a slot which can be communicated with said recess.

In a further preferably embodiment of the invention, said needle retracted trigger can be replaced with a needle carrying member, a tubular front end portion with a flush end or with an end having longitudinally extending gear-like protrusions is exposed after said barrel is fitted with said sealing rubber pad to activate the needle in order to make it be retracted.

According to another aspect of the invention, the present invention provides a needle-retracted controlled safety syringe which comprises a syringe barrel, a needle carrier carrying a needle, a sleeve for covering said needle carrier, a spring, an O-ring and a plunger, wherein a shoulder is formed at the front end of said syringe barrel and is shrunk toward the axial direction of said syringe barrel, a bushing extends forwardly from said shoulder, a flange is formed on a portion of the inner wall of said bushing which is connected to said shoulder, and a snap-on, plug-connected or screw connection structure is provided on the outer wall of said bushing; said needle carrier is of a tubular body having a through hole provided at its centre securing a needle therein, a flaring base is provided at the rear end of said needle carrier, said needle carrier is mounted on the inside of said bushing; said O-ring is arranged on a narrower portion of said flaring base of said needle carrier and is fitted with said flange provided at the inner wall of said bushing so that said needle carrier can be detachably mounted in said bushing; said spring is fitted over said needle carrier, and its rear end is supported on said flaring base of said needle carrier; said sleeve for covering said needle carrier has a cavity opened backwards, the inner diameter of which is set to match to the outer diameter of said bushing, and the inner wall of said sleeve for covering said needle carrier is provided with a snap-on, plug-connected or screw connection structure which can be engaged with said snap-on, plug-connected or screw connection structure provided on the outer wall of said bushing, the closed front end of said sleeve for covering said needle carrier is provided with a needle hole, when said sleeve for covering said needle carrier is snapped, plugged or screwed on said bushing mounted with said needle carrier, the head of said needle can project out of said needle hole, the closed front end of said sleeve for covering said needle carrier can press against the leading end of said spring and pre-compress said spring between said closed front end and said flaring base of said needle carrier; said barrel-like plunger is mounted in said syringe barrel, and when said barrel-like plunger is pushed to the end of a cavity of said syringe barrel, a pushing post or a tubular front end portion of a barrel of said barrel-like plunger urges said O-ring to move entirely or partly so that the fixation of said needle carrier and said bushing is relieved, while the rear end of said syringe barrel relieves the engagement between a supporting member and said barrel present in said barrel-like plunger and releases said supporting member.

As an improvement of the present invention, the needle-retracted controlled safety syringe of the invention comprises a syringe barrel, a needle carrier carrying a needle, a sleeve for covering said needle carrier, a spring, an O-ring and a plunger, wherein a shoulder is formed at the front end of said syringe barrel and is shrunk toward the axial direction of said syringe barrel, a bushing extends forwardly from said shoulder; said needle carrier is of a tubular body having a through hole provided at its centre and securing a needle therein, a flaring base is provided at the rear end of said needle carrier; said sleeve for covering said needle carrier includes a first sleeve which has a closed front end and is provided with a needle hole and a second sleeve, the inner wall of the rear end portion of the second sleeve is provided with a flange, said first sleeve and said second sleeve can be connected as an entirety by means of screw connection, plugging or snapping-in or be connected fixedly by means of adhering or ultrasonic welding; said O-ring is arranged on a narrower portion of said flaring base of said needle carrier and is fitted with said flange provided at the inner wall of said rear end portion of said second sleeve so that said needle carrier can be detachably mounted in said sleeve for covering said needle carrier; said spring is fitted over said needle carrier, and its rear end is supported on said flaring base of said needle carrier; said needle carrier is mounted in said sleeve for covering said needle carrier, the head of said needle can project out of said needle hole formed at the front end of said first sleeve, the closed front end of said first sleeve presses against the leading end of said spring and pre-compresses said spring between said closed front end and said flaring base of said needle carrier; said sleeve for covering said needle carrier is detachably connected to said bushing of said syringe barrel by means of snapping-on, plugging or screw connection; said barrel-like plunger is mounted in said syringe barrel, and when said barrel-like plunger is pushed to the end of a cavity of said syringe barrel, a pushing post or a tubular front end portion of a barrel of said barrel-like plunger urges said O-ring to move entirely or partly so that the fixation of said needle carrier and said sleeve for covering said needle carrier is relieved, while the rear end of said syringe barrel relieves the engagement between a supporting member and said barrel present in said detached barrel-like plunger and releases said supporting member.

As a preferable embodiment of the needle-retracted controlled safety syringe of the invention, the needle hole at the front end of said first sleeve or the needle hole at the front end of said sleeve has an inward flared structure, the front portion of said needle carrier is also provided with a cone-shaped structure, the shape of which matches to the above-mentioned inward flared structure; after the assembly, said needle carrier is fixed by the cooperation between the flared structure of said needle hole and said cone-shaped structure provided at the front portion of said needle carrier.

As a preferable embodiment of the needle-retracted controlled safety syringe of the invention, the syringe comprises a syringe barrel, a needle carrier which carries a needle, a sleeve which covers said needle carrier and a plunger, said plunger comprises a barrel-like plunger comprising a barrel comprising a front portion which is fitted over a sealing rubber pad, a needle retracted trigger and a supporting member, wherein: a slotted hole is disposed at a wall of the front portion of said barrel; a bearing piece is disposed in said slotted hole, one end of said bearing piece is connected to a front side wall of said slotted hole; said bearing piece is deflected laterally towards an interior of said barrel such that said bearing piece is resettable in order to support said needle retracted trigger; said needle retracted trigger is disposed at a front end of a cavity of said barrel and is supported on said bearing piece which has been deflected laterally; said supporting member is disposed in said barrel, a front end of said supporting member supporting said bearing piece which has been deflected laterally, and a rear end of said supporting member comprises a base for sealing the opening at the rear end of said barrel: said barrel and said supporting member each comprising a snap-in structure respectively, which are releasably engaged cooperatively with one another; and said supporting member translates backwards under the action of a needle retraction force so that said bearing piece is returned to a position wherein said needle retracted trigger and said needle are retracted backwards to the interior of said barrel. Said syringe barrel is made of one of glass and cycloolefin copolymers. Said needle carrier, said sleeve which covers said needle carrier and said needle retracted trigger are made of one of stainless steel, glass and cycloolefin copolymers, or are each coated with a layer of polytetrafluoroethylene by means of plating or dipping.

In a further preferable embodiment of the invention, said syringe barrel is formed with a shoulder at its front end, which is shrunk toward the axial direction of said syringe barrel, and from which a bushing extends forward; a flange is provided at the inner wall of a portion of said bushing where said bushing connects to said shoulder, and a snap-on, plug-connected or screw connection structure is provided on the outer wall of said bushing; said needle carrier is in a shape of a tubular body and is mounted within said bushing, said needle carrier comprising a through hole disposed at its center, in which the needle is arranged and fixed, and a flaring base disposed at its rear end; said syringe comprises an O-ring which is nested on a narrower portion of said flaring base of said needle carrier and is fitted with said flange provided at the inner wall of said bushing, so that said needle carrier can be detachably mounted in said bushing; said syringe further comprises a spring which is fitted over said needle carrier with its rear end being supported on said flaring base of said needle carrier; said sleeve which covers said needle carrier has a cavity opened backwards, the inner diameter of which is set to match to the outer diameter of said bushing; and the inner wall of said sleeve which covers said needle carrier is provided with a corresponding snap-on, plug-connected or screw connection structure which can be engaged with the snap-on, plug-connected or screw connection structure disposed on the outer wall of said bushing; a closed front end of said sleeve which covers said needle carrier comprises a needle hole such that when said sleeve which covers said needle carrier is engaged on the bushing which is mounted with the needle carrier by means of snapping, plugging or screw connecting, the head of the needle projects out of the needle hole, and the closed front end of said sleeve which covers said needle carrier presses against the leading end of said spring and thus pre-compresses said spring between said closed front end and said flaring base of said needle carrier; and said barrel-like plunger is mounted within said syringe barrel, and when said plunger is pushed to the end of said cavity of said syringe barrel, the needle retracted trigger, which is mounted on said plunger, urges said O-ring to move entirely or partly so that the fixation of said needle carrier and said bushing can be relieved, and at the same time, the rear end of said syringe barrel relieves the engagement between said supporting member and said barrel present in the barrel-like plunger, and thus release said supporting member.

According to another aspect of the present invention, said sleeve which covers said needle carrier is made of one of polyolefins, polyesters and polyamides.

As a preferable embodiment of the needle-retracted controlled safety syringe of the invention, said syringe barrel is formed with a shoulder at its front end, which is shrunk toward the axial direction of said syringe barrel, and from which a bushing in turn extends forwardly; said needle carrier is in a shape of a tubular body and comprises a through hole disposed at its center, in which the needle is arranged and fixed, and a flaring base disposed at its rear end; said sleeve which covers the needle carrier includes: a first sleeve which comprises a closed front end and is provided with a needle hole; and a second sleeve, the inner wall of which is provided with a flange at its rear end portion, said first sleeve and said second sleeve being connected as an entirety by means of screw connection, plugging or snapping-in or connected fixed by means of adhering or ultrasonic welding; said syringe comprises an O-ring which is nested on a narrower portion of said flaring base of said needle carrier and is engaged with said flange provided at the inner wall of the rear end portion of said second sleeve so that said needle carrier can be detachably mounted in said sleeve which covers said needle carrier;

said syringe further comprises a spring which is fitted over said needle carrier with its rear end being supported on said flaring base of said needle carrier; when said needle carrier is mounted within said sleeve which covers said needle carrier, the head of said needle projects out of said needle hole formed at the front end of said first sleeve, and the closed front end of said first sleeve presses against the leading end of said spring, thus pre-compresses said spring between said closed front end and said flaring base of said needle carrier; said sleeve which covers said needle carrier is detachably connected to said bushing of said syringe barrel by means of snapping-on, plugging-in or screw connecting; said barrel-like plunger is mounted in said syringe barrel, and when said barrel-like plunger is pushed to the end of said cavity of said syringe barrel, the needle retracted trigger which is mounted on said plunger urges said O-ring to move entirely or partly so that the fixation of said needle carrier and said bushing can be relieved and at the same time, the rear end of said syringe barrel relieves the engagement between said supporting member and said barrel present in said barrel-like plunger, and thus release said supporting member; said first sleeve is made of one of polyolefins, polyesters and polyamides; and said second sleeve can be coated on at least one surface with a layer of polytetrafluoroethylene (PTFE) by means of plating or dipping, or is made of one of stainless steel, glass and cycloolefin copolymers.

Alternatively, said second sleeve can be made of one of polyolefins, polyesters and polyamides.

In a preferable embodiment of the needle-retracted controlled safety syringe of the invention, said glass is a borosilicate glass. Said needle carrier, said needle retracted trigger and said sleeve which covers said needle carrier or said second sleeve, which are made of stainless steel, are subjected to passivation treatment or coated with a layer of inert material.

According to a further aspect of the invention, said O-ring and said sealing rubber pad are made of halogenated butyl rubber.

As a preferable embodiment of the needle-retracted controlled safety syringe of the invention, said needle retracted trigger comprises a core bar, which is provided within the cavity formed at the front end of said syringe barrel, and the bear end of which is supported on said bearing piece; and said plunger further comprises a sealing bushing which covers the front end of said core bar and a sleeve for triggering the retraction of said needle carrier, which opens at both ends and covers over said sealing bushing.

In a further embodiment of the invention, said core bar and said sleeve are coated with a layer of polytetrafluoroethylene by means of plating or dipping, or are made of one of stainless steel, glass and cycloolefin copolymers.

According to another aspect of the invention, said glass is a borosilicate glass. Said needle carrier, said sleeve and said sleeve which covers said needle carrier or said second sleeve, which are made of stainless steel, are subjected to passivation treatment or coated with a layer of inert material.

In a further exemplary embodiment of the invention, said O-ring, said sealing rubber pad and said sealing bushing are made of halogenated butyl rubber. Said core bar is made of polypropylene.

Compared to the prior art, the present invention presents the following remarkable and advantageous technical effects:
1. The improved barrel type plunger for use with a needle-retractable safety syringe and the needle-retracted controlled safety syringe containing the above-mentioned barrel type plunger according to the present invention have simper and more reasonable structure, are easy to produce and assemble and can make the controlled retraction of the needle even more convenient.
2. The improved barrel type plunger for use with a needle-retractable safety syringe and the needle-retracted controlled safety syringe containing the above-mentioned barrel type plunger according to the present invention have a even more compact structure so that they can be used for minor milliliter volume syringes having a relatively thinner syringe barrel.
3. The needle-retracted controlled safety syringe containing an improved barrel type plunger according to the present invention can be in contact with the vaccine for a long time, so the syringe of the present invention can be used for the prefilled-vaccine injection.

BRIEF DESCRIPTION OF DRAWINGS

Various exemplary embodiments of the invention will be described in detail with reference to the following figures, wherein:

FIG. 15-1 is a perspective view of the supporting member of the barrel type plunger according to the embodiment 8 of the present invention;

FIG. 16-1 is a perspective view of the barrel of the barrel type plunger according to the embodiment of the present invention;

BEST MODES FOR CARRYING OUT THE INVENTION

Embodiment 1

Figure 1:
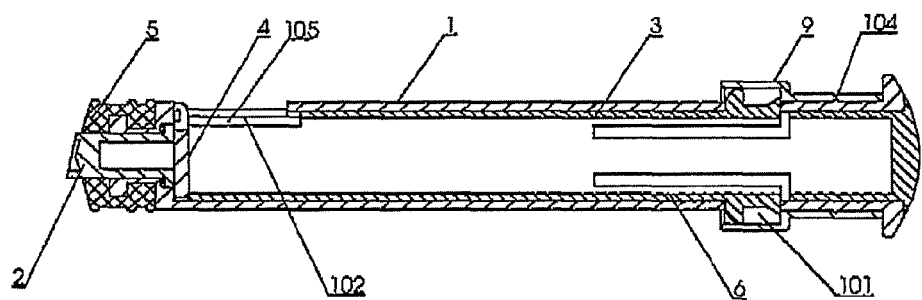
FIG. 1 is a cross sectional view of the improved barrel type plunger for use with a needle-retractable safety syringe according to the embodiment 1 of the present invention.

As shown in FIGS. 1, 2, 9 10 and 17, the improved barrel type plunger for use with a needle-retractable safety syringe according to the embodiment 1 comprises a barrel 1, a needle retracted trigger and a supporting member 3. A head portion of the barrel 1 is fitted with a sealing rubber pad 5.

The needle retracted trigger is a pushing post 2 having a closed front portion. After the assembly, the front end of the pushing post 2 is projected beyond an opening of the barrel cavity formed at the front end of said barrel 1 and the sealing rubber pad 5. Also, the projected portion is in a shape of a tubular structure with a flush end or in a shape of a tubular structure having an end with longitudinally extending gear-like projections.

A slotted hole 102 is provided at a wall of the front portion of said barrel 1. In the slotted hole 102, a bearing piece 4 is provided therein, one end of which is connected to the front side wall of said slotted hole 102. During the assembly, said bearing piece 4 is deflected laterally towards the interior of said barrel 1 in a resettable manner in order to support the needle retracted trigger. The rear portion of the barrel 1 is provided with two opposed windows 101. A flange 104 is formed in a circle on the outer wall of the rear portion of the barrel 1.

The pushing post 2 is provided at a front end of the cavity of the barrel 1 and is supported on the bearing piece 4 which has been deflected laterally.

The supporting member 3 is of a barrel body and is provided in the barrel 1. The front end of the supporting member 3 supports the bearing piece 4 which has been deflected laterally, and the rear end of it is provided with a sealing base 301 for sealing the opening at the rear end of the barrel 1.

A notch 105 adapted for restoring the bearing piece 4 is formed on the wall of the front end portion of the supporting member 3 at a position corresponding to the home position of the bearing piece 4.

On the wall of the rear portion of the supporting member 3, two opposed openings 302 are formed at the positions which correspond to the positions of windows 101, respectively. A flexible rib 6 extending backwards along the axial direction of said barrel body is disposed at the front side wall of each of the openings 302.

The flexible rib 6 is provided with a first projection 601 and a second projection 602 along its length direction. The first projection 601 is in a shape of a block body with a slanted surface formed at its top portion. The second projection 602 is in a shape of triangle.

The distance between the rear end surface of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. Moreover, the projecting height of the second projection 602 is set to be smaller than or equal to the projecting height of the first projection 601. During the assembly, the first projection 601 and the second projection 602 are mounted in the window 101 and extend beyond the same, and the second projection 602 is supported by the rear edge of the window 101. As a result, the supporting member 3 can be releasably engaged in the barrel 1.

Said barrel type plunger also comprises a protective sleeve 9 including a thicker tubing 901 and a thinner tubing 902 which are connected together. The inner diameter of the thicker tubing 901 is set to be larger than or equal to the outer diameter of the syringe barrel of the syringe. The inner diameter of the thinner tubing 902 is set to match to the outer diameter of the barrel 1. A recess 903 which can be engaged to the flange 104 formed at the rear portion of barrel 1 is formed in a circle on the inner wall of the thinner tubing 902. The protective sleeve 9 can be fitted to the rear end of the barrel 1 and can be secured thereon through the engagement of the recess 903 and the flange 104 so that the thicker tubing 901 can surround the first projection 601 and the second projection 602 provided on the flexible rib 6 in order to prevent the barrel type plunger from self-destructing before the use due to the misoperation.

In the present embodiment, the bearing piece 4 provided at the front side wall of the slotted hole 102 may also be made from a part of the wall of the front portion of the barrel 1.

Embodiment 2

As shown in FIGS. 1, 2, 7, 8 and 17, the barrel type plunger for use with the needle-retractable safety syringe according to the present embodiment is substantially the same as that of embodiment 1. The differences between the embodiments 1 and 2 only lie in that, in the present embodiment, there only is one window 101 provided on the wall of the barrel 1 and one opening 302 provided on the wall of the barrel-like supporting member 3, respectively, and there also only is one flexible rib 6.

Embodiment 3

As shown in FIGS. 2, 3, 4 and 17, the barrel type plunger for use with the needle-retractable safety syringe according to the present embodiment is substantially the same as that of embodiment 1. The differences between the embodiments 3 and 1 lie in that, in the present embodiment, there only is one window 101 provided on the wall of the barrel 1 and one opening 302 provided on the wall of the barrel-like supporting member 3, respectively, and there also only is one flexible rib 6. In addition, only a first projection is provided on the flexible rib 6.

The supporting member 3 is in a shape of a barrel body having an opened front end and a closed rear end. On the wall of the rear portion of the barrel body, an opening 302 is disposed. A flexible rib 6 extending forwardly along the axial direction of said barrel body is formed on the rear inner wall of the opening 302. On the outer wall of the flexible rib (6), a first projection 601 is formed in a shape of a block body. A window 101 is provided on the wall of the barrel 1 at a position which corresponds to the position of the first projection 601. During the assembly, the first projection 601 is supported at the rear edge of said window 101 and is projecting beyond the window 101 so that the supporting member 3 can be releasably engaged with said barrel 1.

Figure 28:
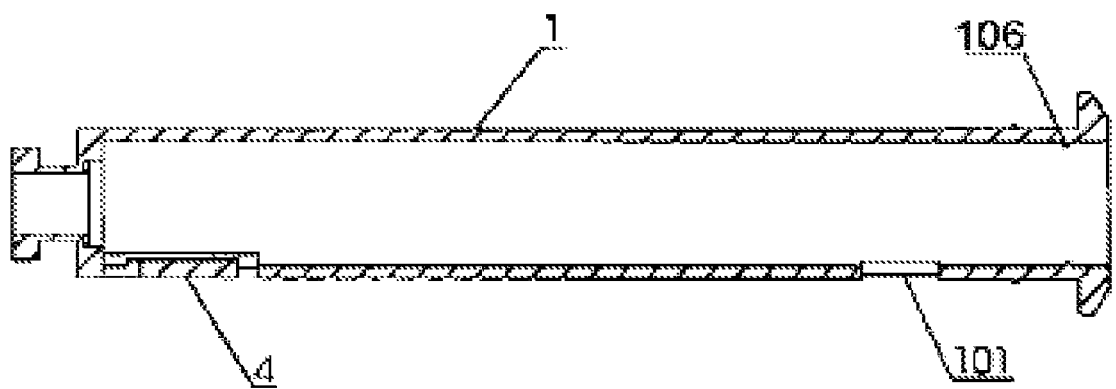
FIG. 28 is a cross sectional view of the barrel of the barrel type plunger according to an embodiment of the present invention.
Figure 29:
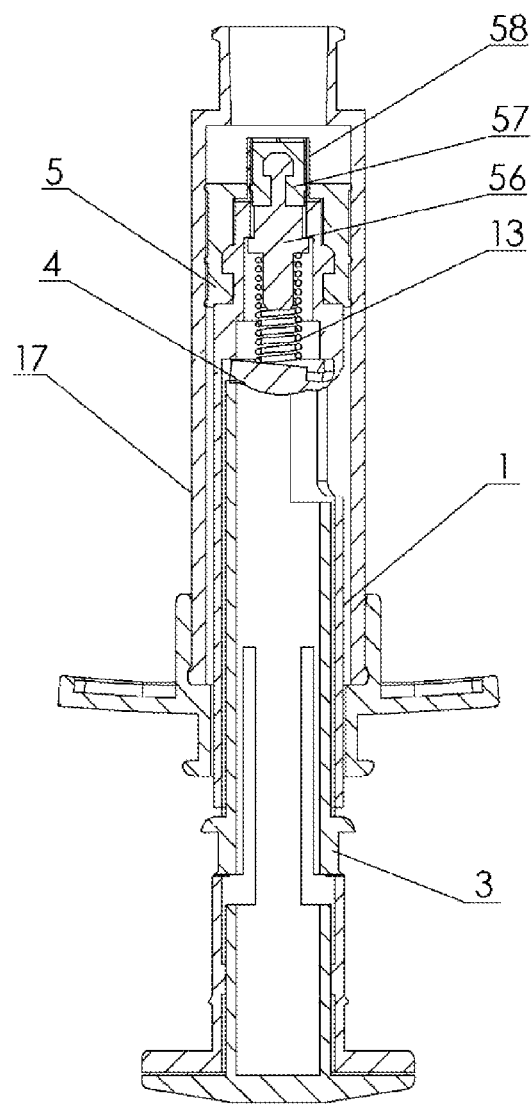
FIG. 29 is a cross sectional view showing the syringe according to the embodiment 19 of the present invention, which does not comprise a needle carrier.
Figure 30:
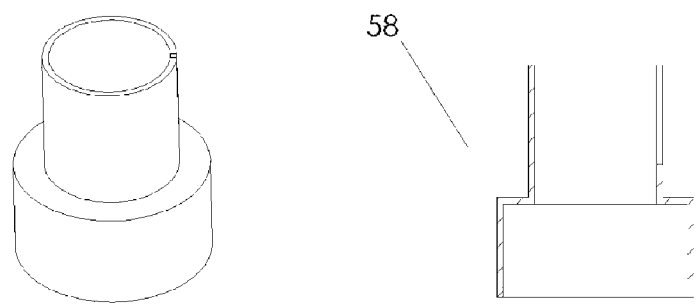
FIG. 30 is a perspective view and a cross sectional view of the sleeve according to the embodiment 19 of the present invention
Figure 31:
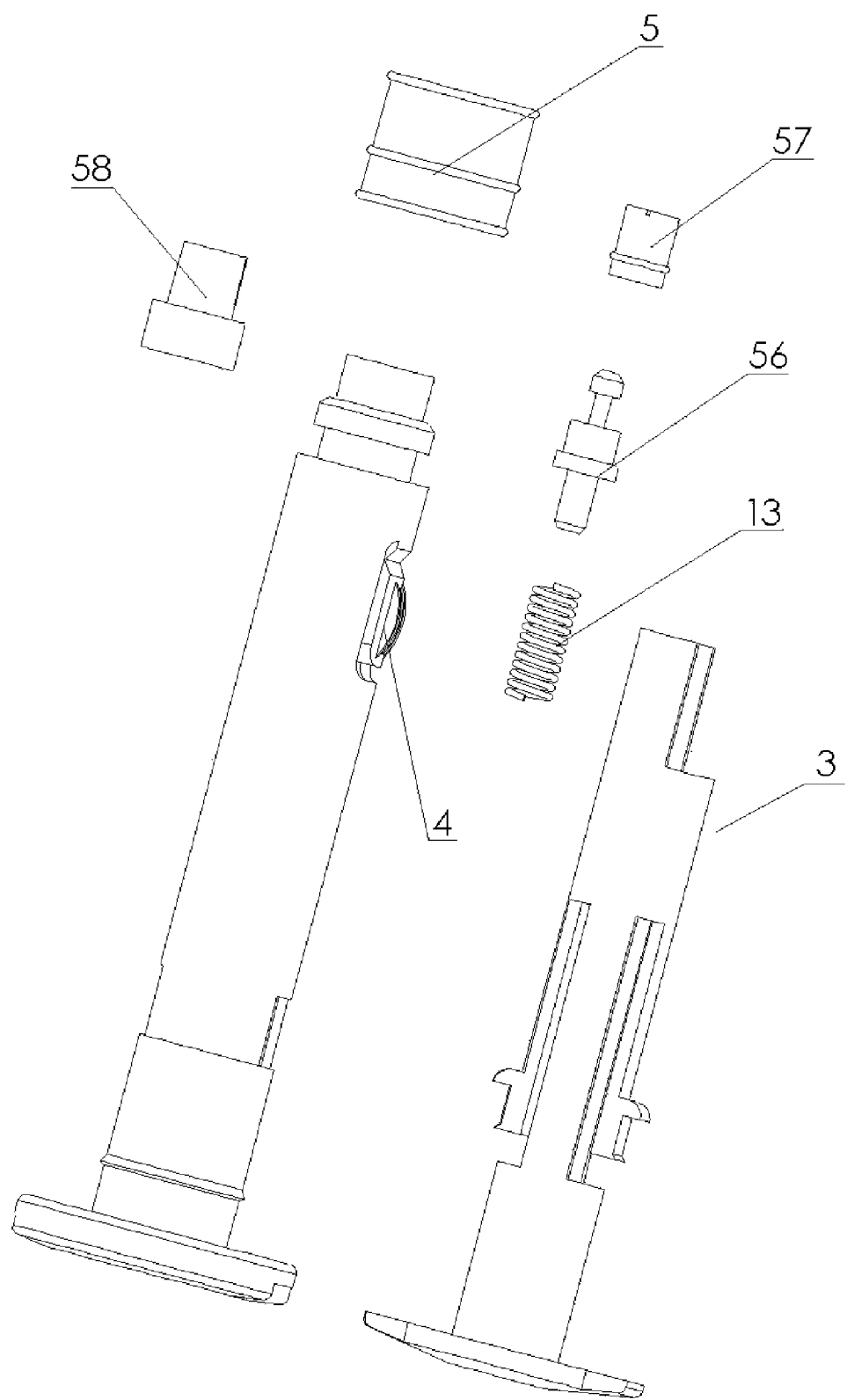
FIG. 31 is an exploded view of the plunger according to embodiment 19 of the present invention.
Figure 32:
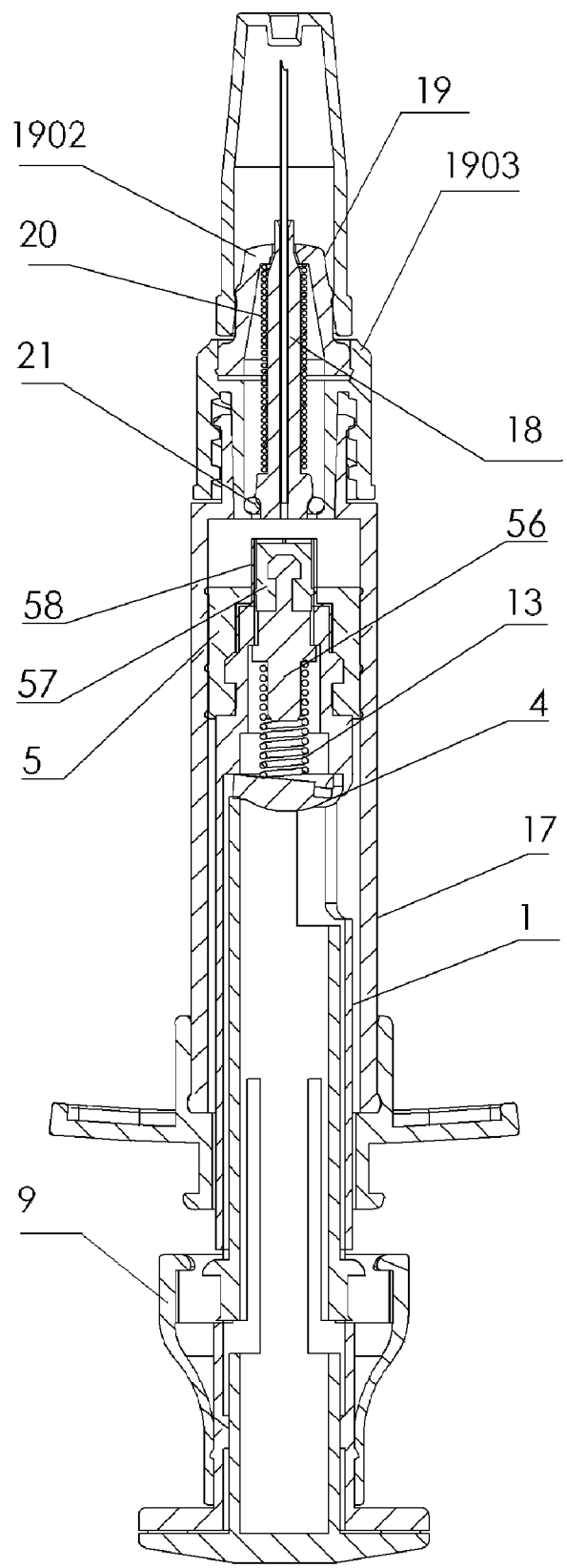
FIG. 32 is a cross sectional view of the syringe according to the embodiment 19 of the present invention, which comprises a protective sleeve.

A projected retaining ring 106 (in FIG. 28) is provided in a circle along the inner wall of the rear portion of the barrel 1 so that the supporting member 3 will be blocked by said retaining ring again after it has been moved backwards to such an extent that said bearing piece 4 has returned to its home position.

In the present embodiment, the first projection 601 can be in a shape of semi-sphere, triangle or any other shape having a slanted top end surface.

Embodiment 4

As shown in FIGS. 1, 2, 5 and 17, the barrel type plunger for use with the needle-retractable safety syringe according to the present embodiment is substantially the same as that of embodiment 3. The differences between the embodiments 3 and 4 lie in the following features:

The outer wall of the flexible rib 6 is further provided with a second projection 602 thereon, which is provided behind the first projection 601. The distance from the rear end surface of the second projection 602 to the rear end surface of the first projection 601 is set to be equal to or larger than the backward movement distance of the supporting member 3 required for returning the bearing piece 4 to the position where the pushing post 2 and the needle can be retracted back to the interior of said barrel 1. In addition, the projecting height of the second projection 602 is set to be smaller than or equal to the projecting height of the first projection 601. During the assembly, the first projection 601 and the second projection 602 are mounted in the window 101 and extend beyond the same, and the second projection 602 is supported by the rear edge of the window 101 so that the supporting member 3 can be releasably engaged in the barrel 1.

Embodiment 5

As shown in FIGS. 1, 2, 6 and 17, the barrel type plunger for use with the needle-retractable safety syringe according to the present embodiment is substantially the same as that of embodiment 3. The differences between the embodiments 3 and 5 lie in the following features:

The supporting member 3 is in a shape of a barrel body. Two opposed openings 302 are formed on the wall of the rear portion of the supporting member 3. A flexible rib 6 extending forwardly along the axial direction of said barrel body is disposed at the rear side wall of each of the openings 302.

Embodiment 6

Figure 11:
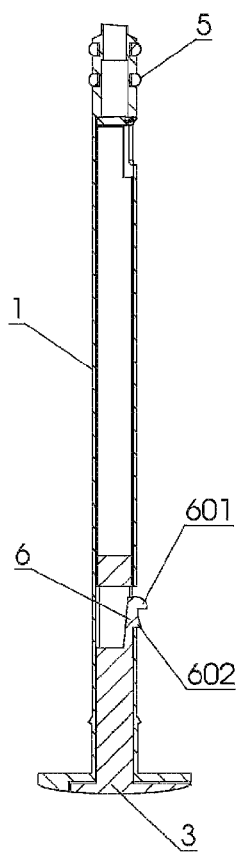
FIG. 11 a cross sectional view of the barrel type plunger according to the embodiment 6 of the present invention.
Figure 12:
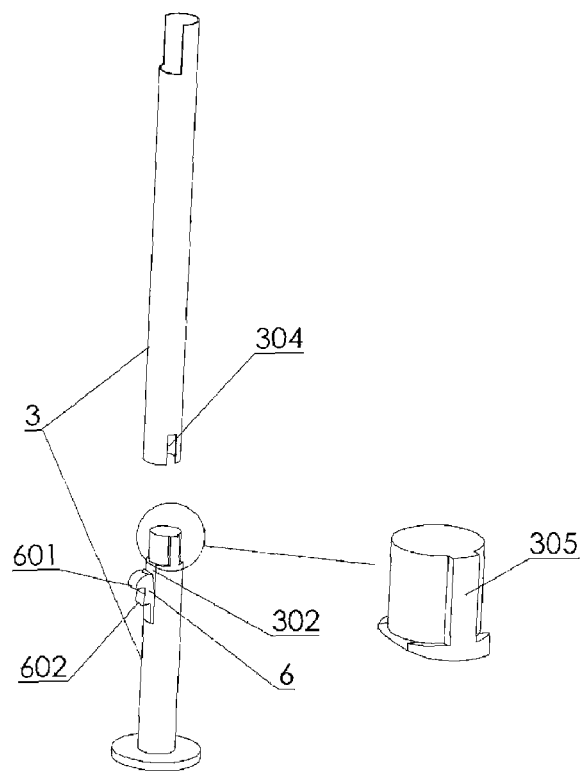
FIG. 12 is a perspective view of the supporting member of the barrel type plunger according to the embodiment 6 of the present invention.

As shown in FIGS. 11 and 12, the barrel type plunger for use with a needle-retractable safety syringe according to the present embodiment comprises a barrel 1, a pushing post 2 and a supporting member 3. The head portion of the barrel 1 is fitted with a sealing rubber pad 5. The structures of the barrel 1, the pushing post 2 and the sealing rubber pad 5 are the same as those of the respective parts of embodiment 4.

The supporting member 3 is composed of a front barrel and a rear barrel which are nested one on the top of another. A notch adapted for restoring the bearing piece 4 is formed on the wall of a front end portion of said front barrel at a position which corresponds to the home position of the bearing piece 4. Additionally, the rear end of said front barrel and the front end of said rear barrel are provided with a socket and spigot joint, respectively, which can be engaged to each other.

A opening 302 is formed on the wall of said rear barrel behind the portion which is jointed to said front barrel. A flexible rib 6 extending backwards along the axial direction of said barrel body is disposed at the front side wall of the opening 302.

The outer diameter of the portion of the front end of said rear barrel which is joined to said front barrel is set to be smaller than the outer diameter of the other portions of said rear barrel and match to the inner diameter of said front barrel. A set piece 305 is disposed on the portion at the front end of said rear barrel which is joined to said front barrel. A locating slot or locating hole 304 adapted for fitting to the set piece 305 is formed on the wall of the portion at the rear end of said front barrel which is joined to said rear barrel.

The flexible rib 6 is provided on its outer wall with a first projection 601 and a second projection 602 which is provided behind the first projection 601. The projecting height of the first projection 601 is set to be larger than or equal to the projecting height of the second projection 602, and the distance between the rear end surface of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. During the assembly, the first projection 601 and the second projection 602 are all mounted in the window 101 and extend beyond the same, and the second projection 602 is supported by the rear edge of the window 101. As a result, the supporting member 3 can be releasably engaged in the barrel 1.

The barrel type plunger according to the present embodiment has more compact structure and therefor is suitable to the minor milliliter volume syringes having a relatively thinner syringe barrel.

Embodiment 7

Figure 13:
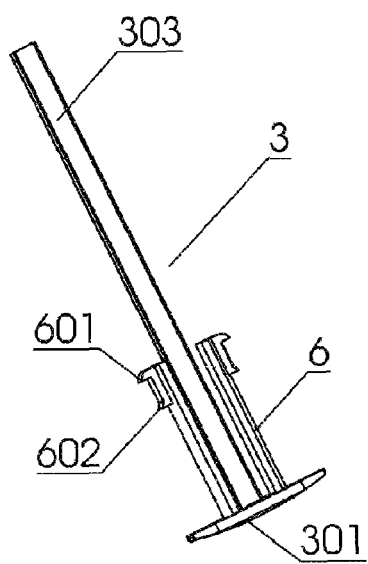
FIG. 13 is a cross sectional view of the supporting member of the barrel type plunger according to the embodiment 7 of the present invention.
Figure 14:
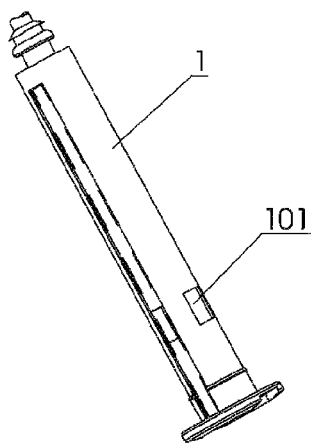
FIG. 14 is a perspective view of the barrel of the barrel type plunger according to the embodiment 7 of the present invention.

As shown in FIGS. 13 and 14, the barrel type plunger for use with the needle-retractable safety syringe according to the present embodiment is substantially the same as that of embodiment 1. The differences between the embodiments 1 and 7 lie in the following features:

The supporting member 3 includes a base 301, two flexible ribs 6 and a supporting bar 303.

The length of the supporting bar 303 is suitable to a position where the bearing piece 4 is in the cavity of the barrel 1 after it has been deflected laterally. The arrangement orientation of the supporting bar 303 on the base 301 is set to match to the arrangement orientation of the bearing piece 4.

On the outer walls of the flexible ribs 6, a first projection 601 is provided, which is in a shape of a block body and has a slanted surface at its top portion. Further, a second projection 602 is provided on the outer walls of the flexible ribs behind the first projection 601. The distance between the rear end of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. The projecting height of the second projection 602 is set to be smaller than or equal to the projecting height of the first projection 601. The first projection 601 and the second projection 602 are all mounted in the windows 101 and extend beyond the same, and the second projection 602 is supported by the rear edge of the window 101. As a result, the supporting member 3 can be releasably engaged in the barrel 1.

An elongated hole for receiving and locating the supporting bar 303 is provided at a portion of the barrel 1 at a position corresponding to the position of the supporting bar 303.

After being deflected laterally, the bearing piece 4 is supported by the front end of the supporting bar 303.

Embodiment 8

Figure 2:
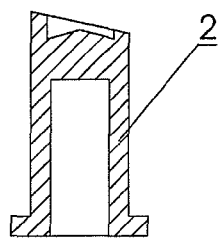
FIG. 2 is a cross sectional view of the pushing post of the barrel type plunger shown in FIG. 1.
Figure 3:
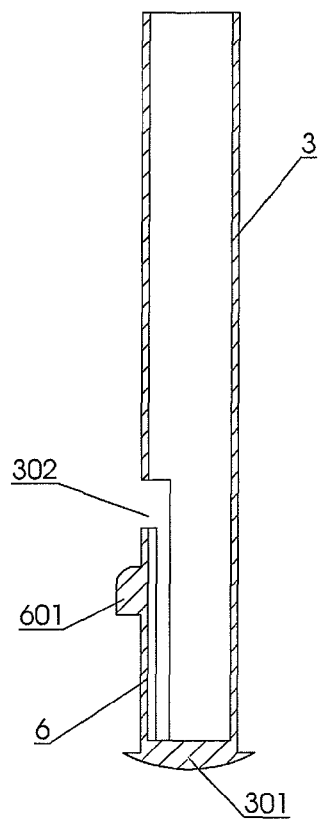
FIG. 3 is a cross sectional view of the supporting member of the barrel type plunger according to the embodiment 3 of the present invention.
Figure 4:
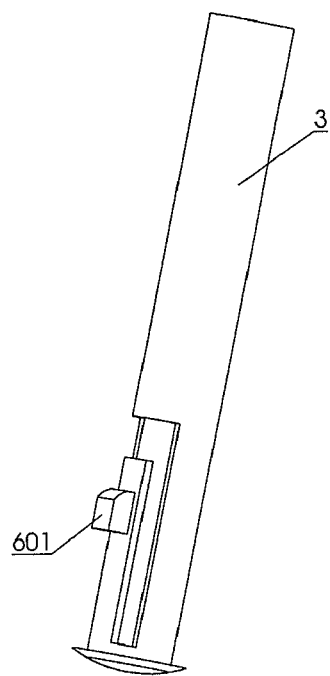
FIG. 4 is a perspective view of the supporting member of the barrel type plunger according to the embodiment 3 of the present invention.
Figure 5:
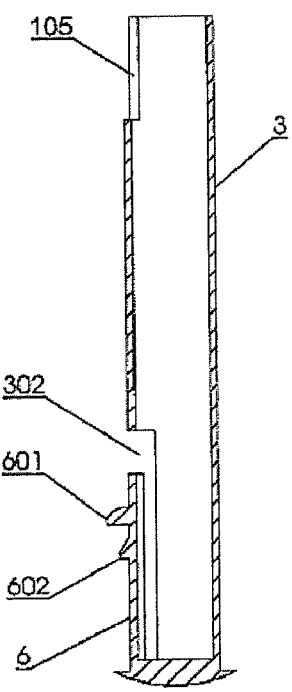
FIG. 5 is a cross sectional view of the supporting member of the barrel type plunger according to the embodiment 4 of the present invention.
Figure 6:
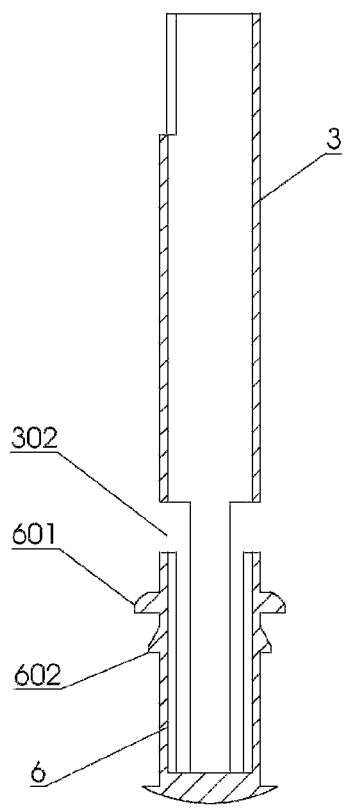
FIG. 6 is a cross sectional view of the supporting member of the barrel type plunger according to the embodiment 5 of the present invention.
Figure 7:
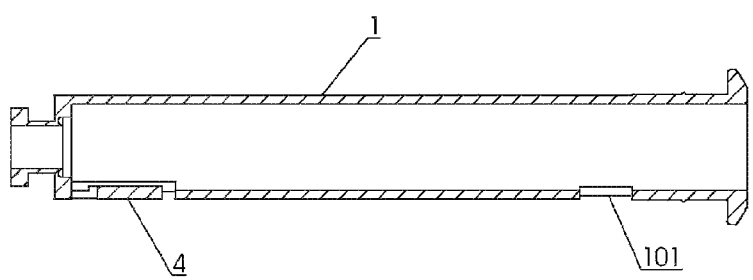
FIG. 7 is a cross sectional view of the barrel of the barrel type plunger according to the embodiment 2 of the present invention.
Figure 8:
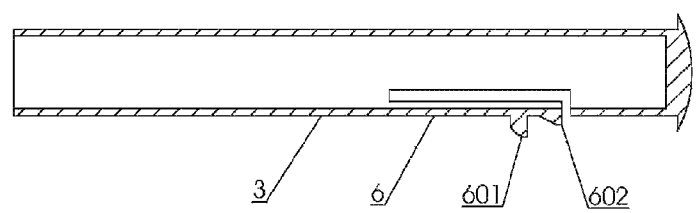
FIG. 8 is a cross sectional view of the supporting member of the barrel type plunger according to the embodiment 2 of the present invention.
Figure 9:
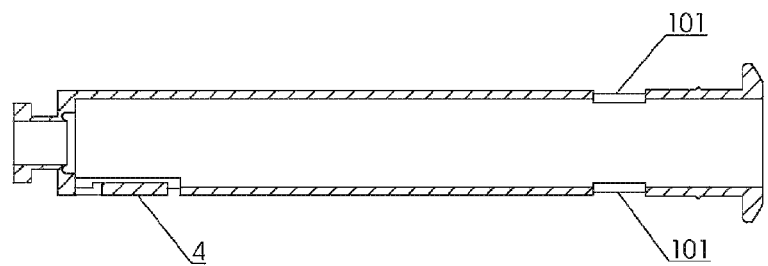
FIG. 9 is a cross sectional view of the barrel of the barrel type plunger according to the embodiments 1 and 9 of the present invention.
Figure 10:
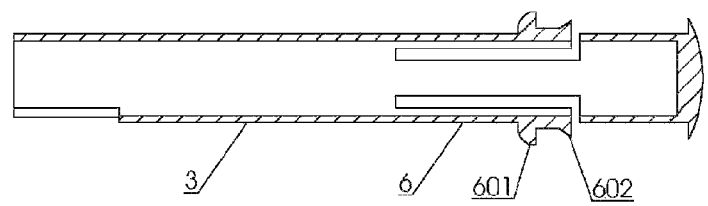
FIG. 10 is a cross sectional view of the supporting member of the barrel type plunger according to the embodiments 1 and 9 of the present invention.
Figure 15:
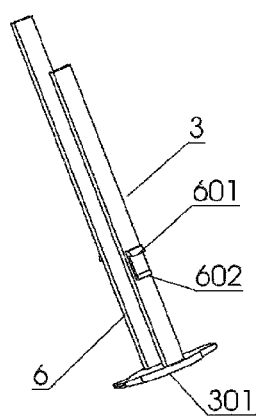
FIG. 15 is a perspective view of the supporting member of the barrel type plunger according to the embodiment 8 of the present invention.
Figures 1, 15:
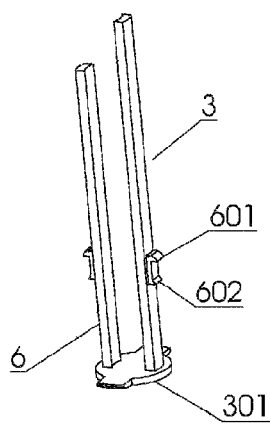
Figure 16:
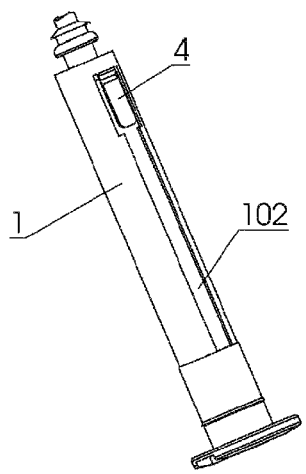
FIG. 16 is a perspective view of the barrel of the barrel type plunger according to the embodiment of the present invention.
Figures 1, 16:
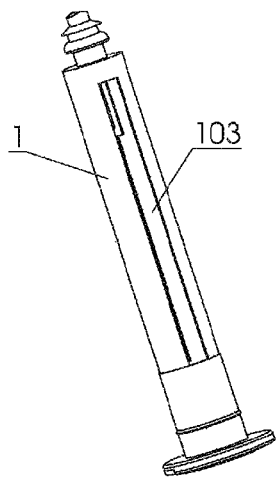

As shown in FIGS. 15, 15-1, 16 and 16-1, the barrel type plunger for use with the needle-retractable safety syringe according to the present embodiment is substantially the same as that of embodiment 7. The differences between the embodiments 7 and 8 lie in the following features:

The slotted hole 102 provided on the wall of the front portion of the barrel 1 extends toward the middle-rear part of the barrel 1. And, a slotted hole 103 is formed on the wall of the barrel 1 opposite to the slotted hole 102. The length of the slotted hole 103 may be set to be equal to that of the slotted hole 102 as shown in FIG. 15-1, or may not be set to be equal to that of the slotted hole 102 as shown in FIG. 15-2.

The supporting member 3 includes a base 301, two flexible ribs 6 and two first projections 601. The two flexible ribs 6 are disposed oppositely on the front end surface of the base 301 and extend forwardly along the axial direction of the barrel 1. The heights and positions of the flexible ribs 6 is set to match to the heights and positions of the slotted hole 102 and the slotted hole 103, respectively.

During the assembly, said two first projections 601 are supported at the respective rear edge of the two slotted holes 102,103, respectively, and are projecting beyond the slotted holes 102,103 so that the supporting member 3 can be releasably engaged in the barrel 1.

On the outer walls of each of the flexible ribs 6, a first projection 601 is provided. A second projection 602 is provided behind each of the first projections 601.

Each of the two first projections 601 is in a shape of a block body and has a slanted surface at its top portion. Further, the shape of each of the second projections 602 is triangular.

The distance between the rear end surface of the first projection 601 and the rear end surface of the second projection 602 is set to be equal to or larger than the backward movement distance of the supporting member 3 required for returning the bearing piece 4 to the position where the pushing post 2 and the needle can be retracted back to the interior of the barrel 1. The projecting height of the second projection 602 is set to be smaller than or equal to the projecting height of the first projection 601. During the assembly, the first projection 601 and the second projection 602 are all mounted in the slotted hole 102 and extend beyond the same, and the second projection 602 is supported by the rear edge of the window 101. As a result, the supporting member 3 can be releasably engaged in the barrel 1.

After being deflected laterally, the bearing piece 4 is supported by the front end of at least one of the flexible ribs.

Embodiment 9

As shown in FIGS. 9, 10, 17, 18 and 21, the barrel type plunger for use with the needle-retractable safety syringe according to the present embodiment is substantially the same as that of embodiment 1. The differences between the embodiments 1 and 9 lie in the following features:

The front portion of the pushing post 2 is provided with a chamber, in which a compressible needle stop member 11 is disposed. The leading end of the needle stop member 11 projects beyond the front end of the pushing post 2 after it has blocked the opening of the chamber of the pushing post 2.

A sealing pad 10 is further arranged between the respective walls of the pushing post 2 and the front end of the barrel 1.

Embodiment 10

Figure 17:
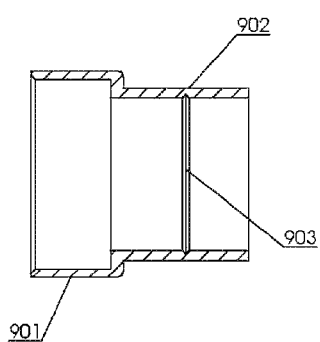
FIG. 17 is a cross sectional view of the protective sleeve according to the various embodiments of the present invention, respectively.
Figure 18:
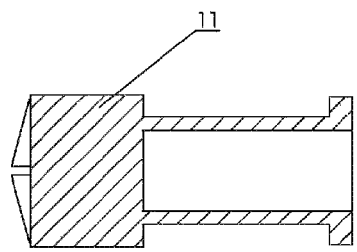
FIG. 18 is a cross sectional view of the needle stop member of the barrel type plunger according to the embodiment 9 of the present invention.
Figure 19:
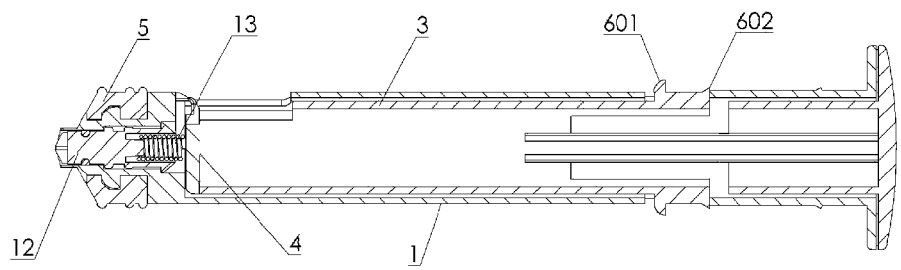
FIG. 19 is a cross sectional view of the barrel type plunger according to the embodiment 10 of the present invention.
Figure 20:
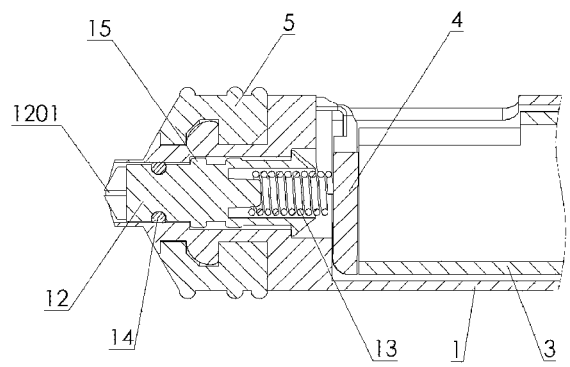
FIG. 20 is an enlarged cross sectional view of the front end of the barrel type plunger according to the embodiment 10 of the present invention.

As shown in FIGS. 17, 19 and 20, the barrel type plunger for use with the needle-retractable safety syringe according to the present embodiment is substantially the same as that of embodiment 9. The differences between the embodiments 9 and 10 lie in the following features:

A tubular front end portion with a flush end or an end having longitudinally extending gear-like protrusions is exposed after the barrel 1 is fitted with a sealing rubber pad 5. The above-mentioned tubular front end portion forms a needle retracted trigger.

The pushing post 2 further comprises a compressible needle stop member 11 which includes a stop post 12 and a spring 13 fitted over the rear portion of said stop post and supporting said stop post.

The cavity provided at the front end of the barrel 1 for arranging the needle stop member 11 includes a front chamber and a rear chamber. The inner diameter of the front chamber is set to match to the outer diameter of the stop post 12, and the inner diameter of the rear chamber is set to be larger than the outer diameter of the stop post 12.

A recess is formed in a circle on the portion of the stop post 12 at a position which corresponds to the position of said front chamber. A sealing ring 14 is disposed in said recess.

A projected orientation ring 15 is formed in at least one circle on a portion of the stop post 12 at such a position that corresponds to the position of said rear chamber. The outer diameter of the orientation ring 15 is set to match to the inner diameter of said rear chamber.

The front end surface of the stop post 12 is provided with a recess 1201. Furthermore, on the wall of the tubular front end portion of the barrel 1 is provided with a slot (not shown in the drawings) which can be communicated with the recess 1201. The leading end of the needle stop member 11 projects out of the front end of the barrel 1 after it has blocked the opening at the front end of the barrel 1. The rear end of the needle stop member 11 can be compressed and supported on the bearing piece 4.

Embodiment 11

The barrel type plunger for use with the needle-retractable safety syringe according to the present embodiment is substantially the same as that of embodiment 1. The differences between the embodiments 1 and 11 lie in the following features:

The needle retracted trigger can be replaced with a needle carrying member.

A tubular front end portion with a flush end or an end having longitudinally extending gear-like protrusions is exposed after the barrel 1 is fitted with the sealing rubber pad 5 in order to activate the needle and make the needle to be retracted. The needle carrying member for carrying the needle is provided in the cavity of the tubular front end portion.

Embodiment 12

Figure 21:
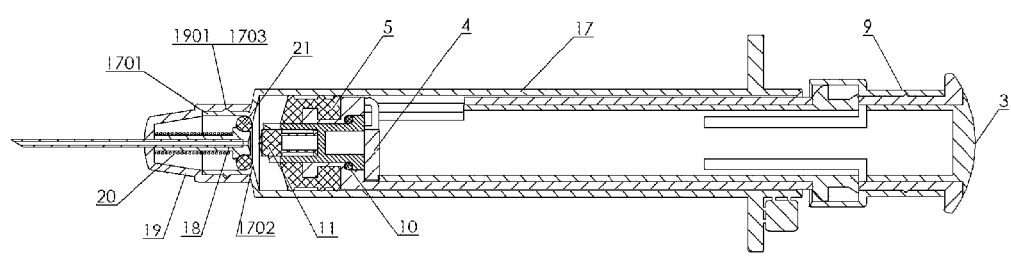
FIG. 21 is a cross sectional view showing the barrel type plunger according to the embodiment 9 of the present invention and the needle-retracted controlled safety syringe according to the embodiment 12 of the present invention.

As shown in FIG. 21, the present embodiment provides a needle-retracted controlled safety syringe which comprises a syringe barrel 17, a needle carrier 18 carrying a needle, a sleeve 19 for covering the needle carrier 18, a spring 20, an O-ring 21 and a barrel-like plunger.

A shoulder is formed at the front end of the syringe barrel 17 and is shrunk toward the axial direction of the syringe barrel 17. A bushing 1701 extends forwardly from said shoulder. A flange 1702 is provided at the inner wall of a portion of the bushing 1701 which is connected to said shoulder. Additionally, a flange 1703 which can be connected to the sleeve 19 for covering the needle carrier 18 is provided on the outer wall of the bushing 1701. The flange 1703 can be replaced with other snap-on, plug-connected or screw connection structure.

The needle carrier 18 is in a shape of a tubular body having a through hole provided at its centre. The needle is arranged in the through hole of the needle carrier 18. A flaring base is provided at the rear end of the needle carrier 18.

The O-ring 21 is arranged on a narrower portion of the flaring base of the needle carrier 18 and is fitted with the flange 1702 provided at the inner wall of the bushing 1701 so that the needle carrier 18 can be detachably mounted in the bushing 1701.

The spring 20 is fitted over the needle carrier 18, and its rear end is supported on the flaring base of the needle carrier 18.

The sleeve 19 for covering the needle carrier 18 has a cavity opened backwards, the inner diameter of which is set to match to the outer diameter of the bushing 1701. The inner wall of the sleeve 19 for covering said needle carrier is provided with a recess 1901 which can be engaged with the flange 1703 provided on the outer wall of the bushing 1701. When the flange 1703 is replaced with other snap-on, plug-connected or screw connection structure, the recess 1901 can be replaced with a snap-on, plug-connected or screw connection structure which can be engaged with the snap-on, plug-connected or screw connection structure that replaced the flange 1703. The closed front end of the sleeve 19 for covering said needle carrier is provided with a needle hole. When the sleeve 19 for covering the needle carrier is engaged on the bushing 1701 mounted with the needle carrier 18, the head of the needle can project out of the needle hole. In the meantime, the closed front end of the sleeve 19 for covering said needle carrier presses against the leading end of the spring 20 and precompresses the spring 20 between the above-mentioned closed front end and the flaring base of the needle carrier 18.

The plunger can be the barrel-like plunger for use with the needle-retractable safety syringe according to the embodiment 9.

The barrel-like plunger is mounted in the syringe barrel 17. When the barrel-like plunger is pushed to the end of a cavity of the syringe barrel 17, the pushing post 2 or the tubular front end portion of the barrel 1 urges the O-ring 21 to move entirely or partly so that the fixation of the needle carrier 18 and the bushing 1701 can be relieved and at the same time, the rear end of the syringe barrel 17 relieves the engagement between the supporting member 3 and the barrel 1 present in the barrel-like plunger.

Embodiment 13

Figure 22:
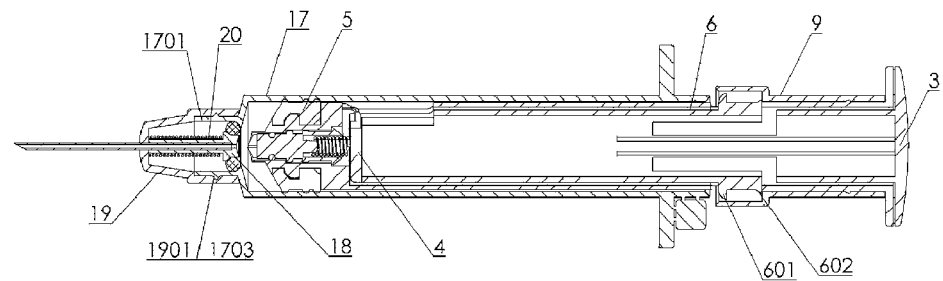
FIG. 22 is a cross sectional view of the needle-retracted controlled safety syringe according to the embodiment 13 of the present invention.

As shown in FIG. 22, the present embodiment provides a needle-retracted controlled safety syringe, the structure of which is substantially the same as that of the needle-retracted controlled safety syringe as described in the embodiment 12. The differences between the needle-retracted controlled safety syringes of embodiments 12 and 13 lie in the following features:

The plunger can be the barrel-like plunger for use with the needle-retractable safety syringe according to the embodiment 10.

The needle hole at the front end of the sleeve 19 for covering said needle carrier has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Embodiment 14

Figure 23:
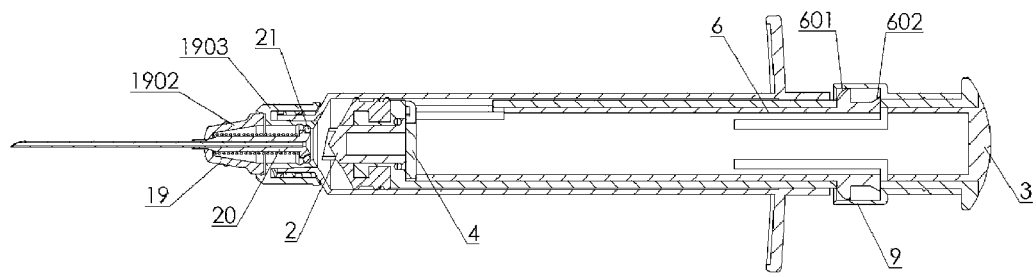
FIG. 23 is a cross sectional view of the needle-retracted controlled safety syringe according to the embodiment 14 of the present invention.
Figure 26:
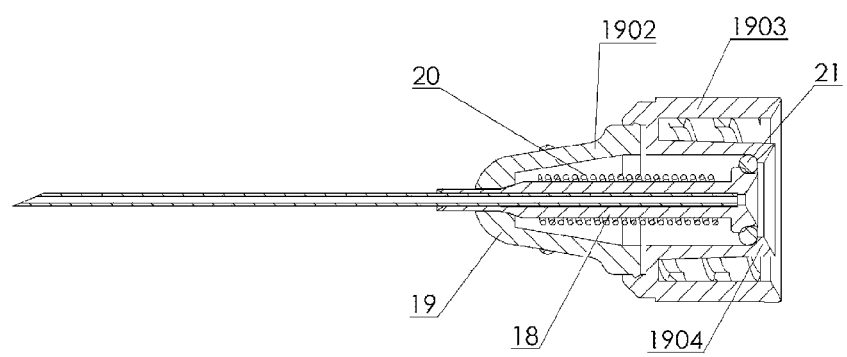
FIG. 26 is an enlarged cross sectional view of the needle head mounted on the needle-retracted controlled safety syringe according to the embodiments 14 and 15 of the present invention.

As shown in FIGS. 23 and 26, the present embodiment provides a needle-retracted controlled safety syringe which comprises a syringe barrel 17, a needle carrier 18 carrying a needle, a sleeve 19 for covering the needle carrier 18, a spring 20, an O-ring 21 and a plunger.

A shoulder is formed at the front end of the syringe barrel 17 and is shrunk toward the axial direction of the syringe barrel 17. A bushing 1701 extends forwardly from the shoulder. The diameter of the bushing 1701 is set to be smaller than the diameter of the syringe barrel 17.

The needle carrier 18 is of a tubular body having a through hole provided at its middle centre. A needle is secured in the through hole of the needle carrier 18. A flaring base is provided at the rear end of the needle carrier 18.

The sleeve 19 for covering the needle carrier 18 includes a first sleeve 1902 which has a closed front end and is provided with a needle hole and a second sleeve 1903. The inner wall of the rear end portion of the second sleeve 1903 is provided with a flange 1904. The first sleeve 1902 and the second sleeve 1903 can be connected as an entirety by means of screw connection, plugging and snapping-in.

The O-ring 21 is arranged on a narrower portion of the flaring base of the needle carrier 18 and is fitted with the flange 1904 provided at the inner wall of the rear end portion of the second sleeve 1903. In this way, the needle carrier 18 can be detachably mounted in the sleeve 19 for covering the needle carrier 18.

The spring 20 is fitted over the needle carrier 18. Also, its rear end is supported on the flaring base of the needle carrier 18.

The needle carrier 18 is mounted in the sleeve 19 for covering said needle carrier. The head of the needle can project out of the needle hole formed at the front end of the first sleeve 1902. The closed front end of the first sleeve 1902 presses against the leading end of the spring 20 and pre-compresses the spring 20 between the closed front end and the flaring base of the needle carrier 18.

The sleeve 19 for covering the needle carrier can be detachably connected to the bushing 1701 of the syringe barrel 17 by means of snapping-on, plugging or screw connection.

The plunger can be the barrel-like plunger for use with the needle-retractable safety syringe according to the embodiment 1.

The barrel-like plunger is mounted in the syringe barrel 17. When the barrel-like plunger is pushed to the end of a cavity of the syringe barrel 17, a front end of the plunger urges the O-ring 21 to move entirely or partly. As a result, the fixation of the needle carrier 18 and the sleeve 19 for covering the needle carrier can be relieved and at the same time, the rear end of the syringe barrel 17 can relieve the engagement between the supporting member 3 and the barrel 1 present in the barrel-like plunger so that the supporting member 3 is released. The needle hole at the front end of the first sleeve 1902 has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Embodiment 15

Figure 24:
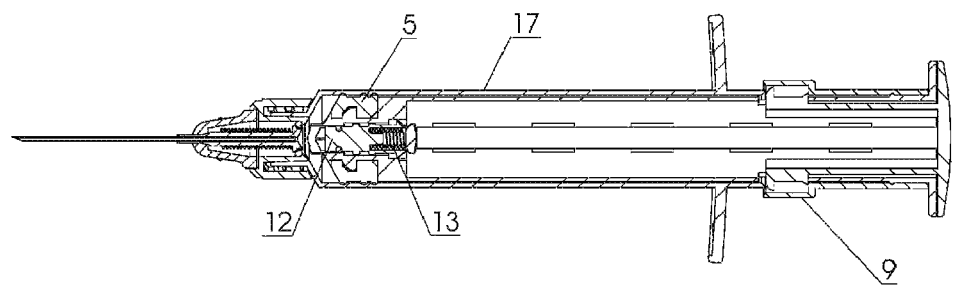
FIG. 24 is a cross sectional view of the needle-retracted controlled safety syringe according to the embodiment 15 of the present invention.
Figure 25:
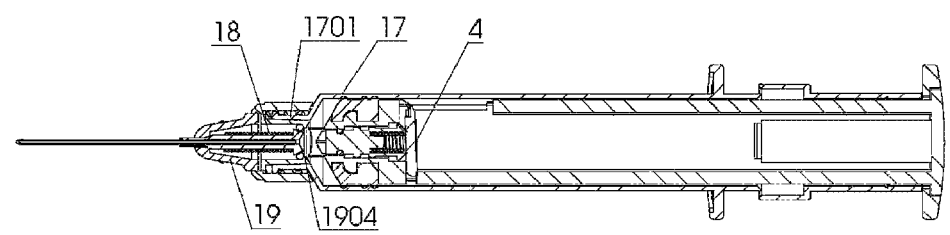
FIG. 25 is a cross sectional view of the needle-retracted controlled safety syringe shown in FIG. 24 taken along the centre line of the same.

As shown in FIGS. 24, 25 and 26, the present embodiment provides a needle-retracted controlled safety syringe, the structure of which is substantially the same as that of the needle-retracted controlled safety syringe as described in the embodiment 14. The differences between the needle-retracted controlled safety syringes of embodiments 14 and 15 lie in the following features:

The plunger can be the barrel-like plunger for use with the needle-retractable safety syringe according to the embodiment 8.

The needle hole at the front end of the first sleeve 1902 has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Embodiment 16

The present embodiment provides a needle-retracted controlled safety syringe, the structure of which is substantially the same as that of the needle-retracted controlled safety syringe as described in the embodiment 14. The differences between the needle-retracted controlled safety syringes of embodiments 14 and 16 lie in the following features:

The plunger can be the barrel-like plunger for use with the needle-retractable safety syringe according to the embodiment 11.

The needle hole at the front end of the sleeve 19 for covering the needle carrier has an inward flared structure. The front portion of the needle carrier 18 is also provided with a cone-shaped structure, the shape of which matches to the above-mentioned inward flared structure. After the assembly, the needle carrier 18 is fixed by the cooperation between the flared structure of the needle hole and the cone-shaped structure provided at the front portion of the needle carrier 18.

Figure 27:
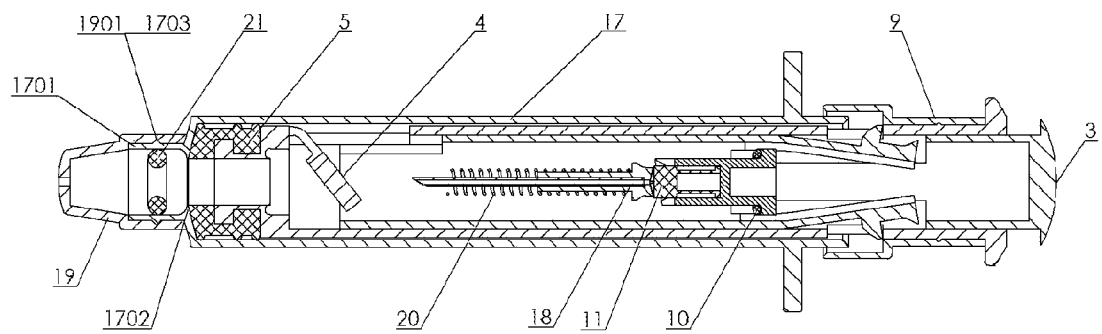
FIG. 27 is a cross sectional view showing the barrel type plunger according to the embodiment 9 of the present invention and the needle-retracted controlled safety syringe according to the embodiment 12 of the present invention under the condition where the needle has been retracted.

Next, the fundamental work principle of the invention will be explained with reference to FIG. 21 and FIG. 27 as an example.

FIG. 21 is a cross sectional view showing the barrel type plunger according to the embodiment 9 of the present invention and the needle-retracted controlled safety syringe according to the embodiment 12 of the present invention. When a user pushes the base 301 of the supporting member 3 in order to push the barrel-like plunger to the end of a cavity at the front end of the syringe barrel 17, the pushing post 2 or the tubular front end portion of the barrel 1 urges the O-ring 21 to move entirely or partly so that the fixation of the needle carrier 18 and the bushing 1701 can be relieved. In the meantime, the flexible rib 6 is deflected towards the interior of the barrel because the first projection 601 receives a backward pressing force from the rear end of the syringe barrel. As a result, the engagement between the supporting member 3 and the barrel 1 is relieved. When the user removes the force acted on the base 301, the backward force exerted by the pre-compressed spring 20 makes the supporting member 3 to move backwards so as to return the bearing piece 4 to its home position, while the needle can be retracted back to the interior of the barrel, as shown in FIG. 27.

Embodiment 17

The present embodiment provides a needle-retracted controlled safety syringe which comprises a syringe barrel 17, a needle carrier 18 which can be fixed with a needle thereon, a sleeve 19 which covers the needle carrier 18, a spring 20, an O-ring 21 and a barrel-like plunger according to the present invention, which can be used to control the retraction of the needle.

A shoulder is formed at the front end of the syringe barrel 17 and is shrunk toward the axial direction of the syringe barrel 17. A bushing 1701 in turn extends forwardly from said shoulder. A flange 1702 is provided at the inner wall of a portion of the bushing 1701, where it is connected to said shoulder. Additionally, a snap-on, plug-connected or screw connection structure 1703 is provided on the outer wall of the bushing 1701.

The needle carrier 18 is in a shape of a tubular body and is mounted within the bushing 1701. The carrier 18 has a through hole disposed at its centre, in which the needle is arranged and fixed. A flaring base is disposed at the rear end of the needle carrier 18.

The O-ring 21 is nested on a narrower portion of the flaring base of the needle carrier 18 and is fitted with the flange 1702 provided at the inner wall of the bushing 1701 so that the needle carrier 18 can be detachably mounted in the bushing 1701.

The spring 20 is fitted over the needle carrier 18 with its rear end being supported on the flaring base of the needle carrier 18.

The sleeve 19 for covering the needle carrier 18 has a cavity opened backwards, the inner diameter of which is set to match to the outer diameter of the bushing 1701. The inner wall of the sleeve 19 for covering said needle carrier is provided with a corresponding snap-on, plug-connected or screw connection structure 1901 which can be engaged with the snap-on, plug-connected or screw connection structure 1703 disposed on the outer wall of the bushing 1701. Additionally, a closed front end of the sleeve 19 which covers the needle carrier 18 comprises a needle hole. When the sleeve 19 which covers the needle carrier is engaged on the bushing 1701 which has already been mounted with the needle carrier 18 by means of snapping, plugging or screw connecting, the head of the needle can project out of the needle hole. In the meantime, the closed front end of the sleeve 19 which covers said needle carrier presses against the leading end of the spring 20 and thus pre-compresses the spring 20 between the above-mentioned closed front end and the flaring base of the needle carrier 18.

The barrel-like plunger according to the invention is mounted in the syringe barrel 17. When the barrel-like plunger is pushed to the end of the cavity of the syringe barrel 17, the needle retracted trigger, e.g. a pushing post 2 or the tubular front end portion of the barrel 1, which is mounted on the plunger, urges the O-ring 21 to move entirely or partly so that the fixation of the needle carrier 18 and the bushing 1701 can be relieved and at the same time, the rear end of the syringe barrel 17 relieves the engagement between the supporting member 3 and the barrel 1 present in the barrel-like plunger, and thus release the supporting member 3.

The syringe barrel 17 can be made of glass or cycloolefine copolymers. Moreover, the needle carrier 18, the sleeve 19 which covers the needle carrier and the needle retracted trigger are coated with a layer of polytetrafluoroethylene (PTFE) by means of plating or dipping, or can be made of a material selected from the group of stainless steel, glass or cycloolefin copolymers.

Alternatively, the sleeve 19 which covers the needle carrier 18 can also be made of the materials commonly used to manufacture syringes, including but not limited to: polyolefins such as homopolymers and copolymers of propylene (e.g., polypropylene, etc), as well as homopolymers and copolymers of ethylene (e.g., polyethylene etc); polyesters such as homopolymers and copolymers of polyacrylate, and homopolymers and copolymers of polycarbonate; and polyamides (transparent polyamides), such as poly-p-phenylene-diacyl trimethyl hexamethylene diamine.

The glass can be borosilicate glass. Additionally, the needle carrier 18, the needle retracted trigger and the sleeve 19 which covers the needle carrier, which are made of stainless steel, can be subjected to passivation treatment or coated with a lay of inert material.

The O-ring 21 and the sealing rubber pad 5 can be made of halogenated butyl rubber.

Embodiment 18

The embodiment 18 provides a needle-retracted controlled safety syringe which comprises a syringe barrel 17, a needle carrier 18 which can be fixed with a needle thereon, a sleeve 19 which covers the needle carrier, a spring 20, an O-ring 21 and a plunger, wherein said plunger is a barrel-like plunger according to the present invention.

A shoulder is formed at a front end of said syringe barrel 17 and is shrunk toward the axial direction of said syringe barrel 17. A bushing 1701 in turns extends forwardly from said shoulder.

The needle carrier 18 is of a tubular body having a through hole which is disposed at its centre and can secure a needle therein. Additionally, a flaring base is disposed at the rear end of the needle carrier 18.

The sleeve 19 which covers the needle carrier 18 includes a first sleeve 1902 which comprises a closed front end and is provided with a needle hole and a second sleeve 1903, the inner wall of which is provided with a flange 1904 at its rear end portion. The first sleeve 1902 and the second sleeve 1903 can be connected as an entirety by means of screw connection, plugging or snapping-in or can be connected fixedly by means of adhering or ultrasonic welding.

The O-ring 21 is nested on a narrower portion of the flaring base of the needle carrier 18 and is engaged with the flange 1904 disposed at the inner wall of the rear end portion of the second sleeve 1903 so that the needle carrier 18 can be detachably mounted in the sleeve 19 which covers the needle carrier 18.

The spring 20 is fitted over the needle carrier 18 with its rear end being supported on the flaring base of the needle carrier 18.

When the needle carrier 18 is mounted within the sleeve 19 which covers the needle carrier, the head of the needle can project out of the needle hole formed at the front end of the first sleeve 1902, and the closed front end of the first sleeve 1902 presses against the leading end of the spring 20, thus pre-compresses the spring 20 between the closed front end and the flaring base of the needle carrier 18;

The sleeve 19 which covers the needle carrier is detachably connected to the bushing 1701 of the syringe barrel 17 by means of snapping-on, plugging-in or screw connecting.

The barrel-like plunger according to the invention is mounted in the syringe barrel 17. When the barrel-like plunger is pushed to the end of the cavity of the syringe barrel 17, the needle retracted trigger, e.g. a pushing post 2 or the tubular front end portion of the barrel 1, which is mounted on the plunger, urges the O-ring 21 to move entirely or partly so that the fixation of the needle carrier 18 and the bushing 1701 can be relieved and at the same time, the rear end of the syringe barrel 17 relieves the engagement between the supporting member 3 and the barrel 1 present in the barrel-like plunger, and thus release the supporting member 3.

The syringe barrel 17 can be made of glass or cycloolefine copolymers, and the needle carrier 18 and the needle retracted trigger can be coated with a layer of polytetrafluoroethylene (PTFE) by means of plating or dipping, or can be made of a material selected from the group of stainless steel, glass or cycloolefin copolymers.

The first sleeve 1902 can be made of a material commonly used for manufacturing syringes, including polyolefins, polyesters and polyamides.

The second sleeve 1903 can be coated on its at least one surface with a layer of polytetrafluoroethylene (PTFE) by means of plating or dipping, or can be made of a material selected from the group of stainless steel, glass or cycloolefin copolymers. Alternatively, the second sleeve 1903 can be made of a material commonly used for manufacturing syringes, including but not limited to: polyolefins, such as homopolymers and copolymers of propylene (e.g., polypropylene, etc.), as well as homopolymers and copolymers of ethylene (e.g., polyethylene, etc.); polyesters, such as homopolymers and copolymers of polyacrylate, and homopolymers and copolymers of polycarbonate; and polyamides (transparent polyamides), such as poly-p-phenylene-diacyl trimethyl hexamethylene diamine.

The glass can be borosilicate glass. Additionally, the needle carrier 18, the needle retracted trigger and the sleeve 19 which covers the needle carrier, which are made of stainless steel, can be subjected to passivation treatment or coated with a lay of inert material.

The O-ring 21 and the sealing rubber pad 5 can be made of halogenated butyl rubber.

Embodiment 19

Embodiment 19 provides a needle-retracted controlled safety syringe, the structure of which is substantially the same as that of the needle-retracted controlled safety syringe described in Embodiment 17 or 18. The present embodiment is characterized by that:

As shown in FIGS. 29-32, the needle retracted trigger consists of a core bar 56, which is disposed within the cavity formed at the front end of the syringe barrel, 1 and the rear end of which is supported on the bearing piece 4.

The barrel-like plunger also includes a sealing bushing 57 which covers the front end of the core bar 56 and a sleeve 58 for triggering the retraction of the needle carrier 18, which opens at both ends and covers over said sealing bushing 57.

Embodiment 20

Embodiment 20 provides a needle-retracted controlled safety syringe, the structure of which is substantially the same as that of the needle-retracted controlled safety syringe described in Embodiment 19. This embodiment 20 is characterized by that: the core bar 56 and the sleeve 58 are coated with a layer of polytetrafluoroethylene by means of plating or dipping, or can be made of stainless steel, glass or cycloolefin copolymers; the glass can be borosilicate glass; the needle carrier 18, the sleeve 58 and the sleeve 19 which covers the needle carrier or the second sleeve 1903, which are made of stainless steel, can be subjected to passivation treatment or coated with a lay of inert material; the O-ring 21, the sealing rubber pad 5 and the sealing bushing 57 can be made of halogenated butyl rubber; and the core bar 56 can be made of polypropylene.

While this invention has been described in conjunction with the exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments of the invention, as set forth above, are intended to be illustrative, not limiting. Various changes may be made without departing from the spirit and scope of the invention. Therefore, the invention is intended to embrace all known or later developed alternatives, modifications, variations, improvements and/or substantial equivalents.

The invention claimed is:

1. A needle-retracted controlled safety syringe, comprising a syringe barrel, a needle carrier which carries a needle, a sleeve which covers said needle carrier and a plunger, wherein:
   said plunger comprises a barrel-like plunger comprising:
      a barrel comprising a front portion which is fitted over a sealing rubber pad;
      a needle retracted trigger; and
      a supporting member;
   wherein:
      a slotted hole is disposed at a wall of the front portion of said barrel;
      a bearing piece is disposed in said slotted hole;
      one end of said bearing piece is connected to a front side wall of said slotted hole;
      said bearing piece is deflected laterally towards an interior of said barrel such that said bearing piece is resettable in order to support said needle retracted trigger;
      said needle retracted trigger is disposed at a front end of a cavity of said barrel and is supported on said bearing piece which has been deflected laterally;
      said supporting member is disposed in said barrel, a front end of said supporting member supporting said bearing piece which has been deflected laterally, and a rear end of said supporting member comprises a base for sealing the opening at the rear end of said barrel;
      said barrel and said supporting member each comprising a snap-in structure respectively, which are releasably engaged cooperatively with one another; and
      said supporting member translates backwards under the action of a needle retraction force so that said bearing piece is returned to a position wherein said needle retracted trigger and said needle are retracted backwards to the interior of said barrel;
   said syringe barrel is made of one of glass and cycloolefin copolymers; and
   said needle carrier, said sleeve which covers said needle carrier and said needle retracted trigger are made of one of stainless steel, glass and cycloolefin copolymers, or are each coated with a layer of polytetrafluoroethylene by means of plating or dipping.

2. The needle-retracted controlled safety syringe according to claim 1, wherein:
   said syringe barrel is formed with a shoulder at its front end, which is shrunk toward the axial direction of said syringe barrel, and from which a bushing extends forward;
   a flange is provided at the inner wall of a portion of said bushing where said bushing connects to said shoulder, and a snap-on, plug-connected or screw connection structure is provided on the outer wall of said bushing;
   said needle carrier is in a shape of a tubular body and is mounted within said bushing, said needle carrier comprising a through hole disposed at its center, in which the needle is arranged and fixed, and a flaring base disposed at its rear end;
   said syringe further comprises:
      an O-ring which is nested on a narrower portion of said flaring base of said needle carrier and is fitted with said flange provided at the inner wall of said bushing, so that said needle carrier can be detachably mounted in said bushing; and
      a spring which is fitted over said needle carrier with its rear end being supported on said flaring base of said needle carrier;
   said sleeve which covers said needle carrier has a cavity opened backwards, the inner diameter of which is set to match to the outer diameter of said bushing; and the inner wall of said sleeve which covers said needle carrier is provided with a corresponding snap-on, plug-connected or screw connection structure which can be engaged with the snap-on, plug-connected or screw connection structure disposed on the outer wall of said bushing;

a closed front end of said sleeve which covers said needle carrier comprises a needle hole such that when said sleeve which covers said needle carrier is engaged on the bushing which is mounted with the needle carrier by means of snapping, plugging or screw connecting, the head of the needle projects out of the needle hole, and the closed front end of said sleeve which covers said needle carrier presses against the leading end of said spring and thus pre-compresses said spring between said closed front end and said flaring base of said needle carrier; and said barrel-like plunger is mounted within said syringe barrel, and when said plunger is pushed to the end of said cavity of said syringe barrel, the needle retracted trigger, which is mounted on said plunger, urges said O-ring to move entirely or partly so that the fixation of said needle carrier and said bushing can be relieved, and at the same time, the rear end of said syringe barrel relieves the engagement between said supporting member and said barrel present in the barrel-like plunger, and thus release said supporting member.

3. The needle-retracted controlled safety syringe according to claim 2, wherein:

said sleeve which covers said needle carrier is made of one of polyolefins, polyesters and polyamides.

4. The needle-retracted controlled safety syringe according to claim 1, wherein:

said syringe barrel is formed with a shoulder at its front end, which is shrunk toward the axial direction of said syringe barrel, and from which a bushing in turn extends forwardly;

said needle carrier is in a shape of a tubular body and comprises a through hole disposed at its center, in which the needle is arranged and fixed, and a flaring base disposed at its rear end;

said sleeve which covers the needle carrier includes: a first sleeve which comprises a closed front end and is provided with a needle hole; and a second sleeve, the inner wall of which is provided with a flange at its rear end portion, said first sleeve and said second sleeve being connected as an entirety by means of screw connection, plugging or snapping-in or connected fixed by means of adhering or ultrasonic welding;

said syringe further comprises:

an O-ring which is nested on a narrower portion of said flaring base of said needle carrier and is engaged with said flange provided at the inner wall of the rear end portion of said second sleeve so that said needle carrier can be detachably mounted in said sleeve which covers said needle carrier; and a spring which is fitted over said needle carrier with its rear end being supported on said flaring base of said needle carrier;

when said needle carrier is mounted within said sleeve which covers said needle carrier, the head of said needle projects out of said needle hole formed at the front end of said first sleeve, and the closed front end of said first sleeve presses against the leading end of said spring, thus pre-compresses said spring between said closed front end and said flaring base of said needle carrier;

said sleeve which covers said needle carrier is detachably connected to said bushing of said syringe barrel by means of snapping-on, plugging-in or screw connecting;

said barrel-like plunger is mounted in said syringe barrel, and when said barrel-like plunger is pushed to the end of said cavity of said syringe barrel, the needle retracted trigger which is mounted on said plunger urges said O-ring to move entirely or partly so that the fixation of said needle carrier and said bushing can be relieved and at the same time, the rear end of said syringe barrel relieves the engagement between said supporting member and said barrel present in said barrel-like plunger, and thus release said supporting member;

said first sleeve is made of one of polyolefins, polyesters and polyamides; and said second sleeve can be coated on at least one surface with a layer of polytetrafluoroethylene (PTFE) by means of plating or dipping, or is made of one of stainless steel, glass and cycloolefin copolymers.

5. The needle-retracted controlled safety syringe according to claim 4, wherein:

said second sleeve is made of one of polyolefins, polyesters and polyamides.

6. The needle-retracted controlled safety syringe according to any one of claims 1-4, wherein:

said glass is a borosilicate glass; and said needle carrier, said needle retracted trigger and said sleeve which covers said needle carrier or said second sleeve, which are made of stainless steel, are subjected to passivation treatment or coated with a layer of inert material.

7. The needle-retracted controlled safety syringe according to claim 6, wherein:

said O-ring and said sealing rubber pad are made of halogenated butyl rubber.

8. The needle-retracted controlled safety syringe according to any one of claims 1-4, wherein:

said needle retracted trigger comprises a core bar, which is provided within the cavity formed at the front end of said syringe barrel, and the bear end of which is supported on said bearing piece; and said plunger further comprises: a sealing bushing which covers the front end of said core bar; and a sleeve for triggering the retraction of said needle carrier, which opens at both ends and covers over said sealing bushing.

9. The needle-retracted controlled safety syringe according to claim 8, wherein:

said core bar and said sleeve are coated with a layer of polytetrafluoroethylene by means of plating or dipping, or are made of one of stainless steel, glass and cycloolefin copolymers.

10. The needle-retracted controlled safety syringe according to claim 9, wherein:

said glass is a borosilicate glass; and said needle carrier, said sleeve and said sleeve which covers said needle carrier or said second sleeve, which are made of stainless steel, are subjected to passivation treatment or coated with a layer of inert material.

11. The needle-retracted controlled safety syringe according to claim 10, wherein:

said O-ring, said sealing rubber pad and said sealing bushing are made of halogenated butyl rubber; and said core bar is made of polypropylene.

* * * * *